US012673161B2

(12) United States Patent     (10) Patent No.:   US 12,673,161 B2

Price et al.     (45) Date of Patent:     Jul. 7, 2026

---

(54) BFS INJECTION AND CONNECTION ASSEMBLIES

(71) Applicant: Koska Family Limited, East Sussex (GB)

(72) Inventors: Jeff Price, Windermere, FL (US); Eric Dwyer Gibney, West Chester, PA (US)

(73) Assignee: ApiJect, Stamford, CT (US)

( * ) Notice: Subject to any disclaimer, the term of this patent is extended or adjusted under 35 U.S.C. 154(b) by 602 days.

(21) Appl. No.: 18/055,103

(22) Filed: Nov. 14, 2022

(65)      Prior Publication Data

US 2023/0141404 A1     May 11, 2023

Related U.S. Application Data

(63) Continuation of application No. PCT/US2022/049608, filed on Nov. 10, 2022.

(60) Provisional application No. 63/400,898, filed on Aug. 25, 2022, provisional application No. 63/278,469, filed on Nov. 11, 2021.

(51) Int. Cl.
    *A61M 5/178*     (2006.01)
    *A61J 1/20*     (2006.01)
    *A61M 5/32*     (2006.01)

(52) U.S. Cl.
    CPC .......... *A61M 5/178* (2013.01); *A61M 5/3202* (2013.01); *A61J 1/2006* (2015.05)

(58) Field of Classification Search
    CPC ..... A61M 5/178; A61M 5/3202; A61J 1/2006
    See application file for complete search history.

(56)      References Cited

U.S. PATENT DOCUMENTS

| | | | |
|---|---|---|---|
| 2,667,165 | A | 1/1954 | Smith |
| 2,717,598 | A | 9/1955 | Krasno |
| 2,737,948 | A * | 3/1956 | Brown .................. A61M 5/288 |
| | | | 604/274 |
| 2,828,743 | A | 4/1958 | Ashkenaz |
| 3,073,307 | A | 1/1963 | Stevens |
| 3,192,925 | A | 7/1965 | Cunningham |
| 3,251,915 | A | 5/1966 | Pechthold |
| 3,406,686 | A | 10/1968 | Keller |
| 3,491,757 | A | 1/1970 | Arce |
| 3,640,388 | A | 2/1972 | Ferrari |
| 3,917,120 | A | 11/1975 | Larenz |
| 3,989,045 | A | 11/1976 | Van Eck |

(Continued)

FOREIGN PATENT DOCUMENTS

| | | |
|---|---|---|
| AU | 2337470 | 6/1972 |
| AU | 2019203408 B2 | 9/2020 |

(Continued)

OTHER PUBLICATIONS

Office Action for Chinese Application 201880087016.7 dated Sep. 14, 2021; 3 pps.

(Continued)

*Primary Examiner* — Dung T Ulsh

(74) *Attorney, Agent, or Firm* — Rowan Tree Law Group, PLLC; Carson C.K. Fincham

(57)       ABSTRACT

A pre-filled medical delivery system assembled and configured to allow delivery of a single dose of a therapeutic agent (e.g., vaccine, drug, medicament, etc.) from a Blow-Fill-Seal (BFS) bottle to a patient utilizing one or more BFS injection or connection assemblies.

12 Claims, 15 Drawing Sheets

(56)                    References Cited

U.S. PATENT DOCUMENTS

| | | | |
|---|---|---|---|
| 4,018,222 A | 4/1977 | Mcaleer | |
| 4,022,206 A | 5/1977 | Hilleman | |
| 4,058,121 A | 11/1977 | Choksi | |
| 4,130,117 A | 12/1978 | Van Eck | |
| 4,502,616 A | 3/1985 | Meierhoefer | |
| 4,539,172 A | 9/1985 | Winchell | |
| 4,643,309 A | 2/1987 | Evers | |
| 4,671,763 A | 6/1987 | Weiler | |
| 4,883,473 A | 11/1989 | Thomas | |
| 4,955,871 A | 9/1990 | Thomas | |
| 4,966,581 A | 10/1990 | Sergio | |
| 4,979,630 A | 12/1990 | Rose | |
| 4,995,519 A | 2/1991 | Rose | |
| 5,112,311 A | 5/1992 | Utterberg | |
| 5,135,514 A | 8/1992 | Kimber | |
| 5,139,489 A | 8/1992 | Hollister | |
| 5,217,480 A | 6/1993 | Haber | |
| 5,222,948 A | 6/1993 | Austin | |
| 5,242,422 A | 9/1993 | Schneberger | |
| 5,261,881 A | 11/1993 | Riner | |
| 5,356,052 A | 10/1994 | Poynter | |
| 5,370,626 A | 12/1994 | Farris | |
| 5,374,263 A | 12/1994 | Weiler | |
| 5,395,365 A | 3/1995 | Weiler | |
| 5,409,125 A | 4/1995 | Kimber | |
| 5,427,275 A | 6/1995 | Hansen | |
| 5,503,885 A | 4/1996 | Anderson | |
| 5,509,906 A | 4/1996 | Poynter | |
| 5,533,505 A | 7/1996 | Kaellstrand | |
| 5,624,407 A | 4/1997 | Claro | |
| 5,636,640 A | 6/1997 | Staehlin | |
| 5,761,885 A | 6/1998 | Hansen | |
| 5,944,699 A * | 8/1999 | Barrelle | A61M 5/34 |
| | | | 604/263 |
| 6,050,400 A | 4/2000 | Taskis | |
| D425,617 S | 5/2000 | Snedden | |
| 6,065,270 A | 5/2000 | Reinhard | |
| 6,068,148 A | 5/2000 | Weiler | |
| 6,120,478 A | 9/2000 | Moore | |
| 6,134,866 A | 10/2000 | Schoenewolff | |
| 6,173,852 B1 | 1/2001 | Browne | |
| 6,200,296 B1 | 3/2001 | Dibiasi | |
| 6,231,559 B1 | 5/2001 | Loretti | |
| 6,241,124 B1 | 6/2001 | Hoyt | |
| 6,258,063 B1 | 7/2001 | Haar | |
| D447,560 S | 9/2001 | Hellberg | |
| 6,332,876 B1 | 12/2001 | Poynter | |
| 6,357,626 B1 | 3/2002 | Zhang | |
| 6,379,342 B1 | 4/2002 | Levinson | |
| 6,383,166 B1 | 5/2002 | Farris | |
| D458,366 S | 6/2002 | Hellberg | |
| D462,760 S | 9/2002 | Ahlgrim | |
| D467,336 S | 12/2002 | Gilbard | |
| 6,517,768 B1 | 2/2003 | Weiler | |
| D471,628 S | 3/2003 | Louviere | |
| 6,585,134 B2 | 7/2003 | Farris | |
| 6,626,308 B2 | 9/2003 | Weiler | |
| D492,407 S | 6/2004 | Masuda | |
| 6,764,463 B1 | 7/2004 | Farris | |
| 6,777,052 B2 | 8/2004 | Kai | |
| 6,860,405 B1 | 3/2005 | Poynter | |
| 6,918,418 B1 | 7/2005 | Farris | |
| D517,207 S | 3/2006 | Poynter | |
| 7,028,862 B2 | 4/2006 | Poynter | |
| 7,029,465 B2 | 4/2006 | Heyes | |
| 7,100,600 B2 | 9/2006 | Loeffler | |
| 7,188,750 B2 | 3/2007 | Vogel | |
| 7,308,782 B2 | 12/2007 | Hansen | |
| 7,357,893 B2 | 4/2008 | Hansen | |
| D573,710 S | 7/2008 | Goodman | |
| 7,425,207 B2 | 9/2008 | Miller | |
| 7,438,704 B1 | 10/2008 | Kawashima | |
| 7,487,894 B2 | 2/2009 | Zahn | |
| 7,513,397 B2 | 4/2009 | Zahn | |
| 7,562,796 B2 | 7/2009 | Zahn | |
| 7,632,253 B2 | 12/2009 | Tetsuya | |
| D618,339 S | 6/2010 | Hansen | |
| 7,832,594 B2 | 11/2010 | Yamada | |
| 7,832,601 B2 | 11/2010 | Zahn | |
| 7,866,514 B1 | 1/2011 | Hansen | |
| 7,883,660 B2 | 2/2011 | Matsuda | |
| 7,892,211 B2 | 2/2011 | McCulloch | |
| 7,892,614 B2 | 2/2011 | Radermacher | |
| 7,993,304 B2 | 8/2011 | Kriesel | |
| 8,087,524 B2 | 1/2012 | Hansen | |
| 8,133,202 B2 | 3/2012 | Marsh | |
| D674,481 S | 1/2013 | Decoste | |
| 8,377,029 B2 | 2/2013 | Nagao | |
| D681,196 S | 4/2013 | Henrikson | |
| 8,431,068 B2 | 4/2013 | Hansen | |
| 8,434,643 B2 | 5/2013 | Harris | |
| 8,464,918 B1 | 6/2013 | Harris | |
| 8,486,043 B2 | 7/2013 | Iyer | |
| 8,486,501 B2 | 7/2013 | Manabe | |
| 8,551,053 B2 | 10/2013 | Hansen | |
| 8,640,873 B2 | 2/2014 | Nakano | |
| 8,652,096 B2 | 2/2014 | Alvey | |
| 8,663,188 B2 | 3/2014 | Genosar | |
| 8,672,885 B2 | 3/2014 | Kriesel | |
| D710,993 S | 8/2014 | Decoste | |
| 8,795,226 B2 | 8/2014 | Kuhn | |
| 8,857,470 B2 | 10/2014 | Rahimy | |
| D721,434 S | 1/2015 | Mulvey | |
| 8,967,140 B2 | 3/2015 | Denyer | |
| 8,986,236 B2 | 3/2015 | Slokovic | |
| D731,642 S | 6/2015 | Cehajic | |
| 9,079,686 B2 | 7/2015 | Domkowski | |
| 9,095,500 B2 | 8/2015 | Brandenburger | |
| 9,108,777 B1 | 8/2015 | Santamarta | |
| 9,132,238 B2 | 9/2015 | Ferreri | |
| 9,150,317 B2 | 10/2015 | Hansen | |
| 9,168,201 B2 | 10/2015 | Mcaffer | |
| 9,216,477 B2 | 12/2015 | Gibson | |
| 9,242,051 B2 | 1/2016 | Jugl | |
| 9,248,076 B2 | 2/2016 | Sullivan | |
| 9,265,889 B2 | 2/2016 | Thornton | |
| D753,292 S | 4/2016 | Oates, II | |
| 9,314,403 B2 | 4/2016 | Smith | |
| 9,358,738 B2 | 6/2016 | Wolters | |
| 9,364,393 B1 | 6/2016 | Grabowski | |
| 9,399,102 B2 | 7/2016 | Dewoolfson | |
| 9,526,839 B2 | 12/2016 | Chia | |
| D776,266 S | 1/2017 | Dombrowski | |
| 9,533,065 B2 | 1/2017 | Foreman | |
| D779,653 S | 2/2017 | Habig | |
| 9,592,354 B2 | 3/2017 | Sullivan | |
| 9,597,259 B2 | 3/2017 | Becker | |
| 9,737,664 B2 | 8/2017 | Gardner | |
| 9,808,608 B2 | 11/2017 | Webb | |
| 9,820,913 B2 | 11/2017 | Genosar | |
| 9,828,148 B2 | 11/2017 | Schreckenhoefer | |
| 9,908,682 B2 | 3/2018 | Mcaffer | |
| 9,918,900 B2 | 3/2018 | Hansen | |
| 9,987,790 B2 | 6/2018 | Suyama | |
| 10,018,536 B2 | 7/2018 | Huschke | |
| 10,039,884 B2 | 8/2018 | Ferreri | |
| 10,064,785 B2 | 9/2018 | Spallek | |
| 10,086,984 B2 | 10/2018 | Colangelo | |
| 10,098,814 B2 | 10/2018 | Spallek | |
| 10,105,491 B2 | 10/2018 | Gelblum | |
| 10,117,994 B2 | 11/2018 | Holtwick | |
| 10,118,000 B2 | 11/2018 | Schraga | |
| 10,147,268 B2 | 12/2018 | Walker | |
| 10,149,939 B2 | 12/2018 | Giambattista | |
| 10,155,088 B2 | 12/2018 | Basile | |
| 10,155,829 B2 | 12/2018 | Destro | |
| 10,207,053 B2 | 2/2019 | Groskopf | |
| 10,278,896 B2 | 5/2019 | Brandenburger | |
| 10,315,788 B2 | 6/2019 | Consolaro | |
| 10,335,507 B2 | 7/2019 | Reed | |
| 10,342,735 B2 | 7/2019 | Chou | |
| 10,351,272 B2 | 7/2019 | Colangelo | |
| 10,363,369 B2 | 7/2019 | Cosman | |
| D859,647 S | 9/2019 | Chang | |

(56) References Cited

U.S. PATENT DOCUMENTS

| 10,456,328 | B2 | 10/2019 | Brandenburger |
| 10,464,708 | B2 | 11/2019 | Geser |
| 10,471,244 | B2 | 11/2019 | Dombrowski |
| 10,500,338 | B2 | 12/2019 | Berenshteyn |
| 10,512,591 | B2 | 12/2019 | Oshgan |
| 10,525,212 | B2 | 1/2020 | Thornton |
| 10,543,317 | B2 | 1/2020 | Basile |
| 10,543,944 | B2 | 1/2020 | Batema |
| 10,583,256 | B2 | 3/2020 | Berry |
| 10,589,075 | B2 | 3/2020 | Wills |
| 10,639,839 | B2 | 5/2020 | Consolaro |
| 10,716,901 | B2 | 7/2020 | Genosar |
| 10,737,840 | B2 | 8/2020 | Oates, II |
| 10,765,849 | B2 | 9/2020 | Chiang |
| D898,901 | S | 10/2020 | De Malibran-Santibanez |
| 10,793,323 | B2 | 10/2020 | Cosman |
| 10,821,053 | B2 | 11/2020 | Rajagopal |
| 10,828,860 | B2 | 11/2020 | Vaes |
| 10,874,588 | B2 | 12/2020 | Schabbach |
| 10,888,454 | B2 | 1/2021 | Ivri |
| 10,918,809 | B2 | 2/2021 | Ferreri |
| 10,928,236 | B2 | 2/2021 | Adler |
| 10,933,190 | B2 | 3/2021 | Berry |
| 10,940,633 | B2 | 3/2021 | Schubert |
| 10,961,003 | B2 | 3/2021 | Banuelos |
| 10,967,126 | B2 | 4/2021 | Holtwick |
| 10,981,713 | B2 | 4/2021 | Genosar |
| 11,027,862 | B2 | 6/2021 | Wong |
| 11,059,638 | B2 | 7/2021 | Spallek |
| 11,077,263 | B2 | 8/2021 | Loenner |
| 11,123,499 | B2 | 9/2021 | Basile |
| 11,136,148 | B2 | 10/2021 | Rehbein |
| 11,167,889 | B2 | 11/2021 | Naohiro |
| 11,173,022 | B2 | 11/2021 | De Malibran-Santibanez |
| 11,185,634 | B2 | 11/2021 | Genosar |
| 11,191,910 | B2 | 12/2021 | Hoekman |
| 11,198,243 | B2 | 12/2021 | Beck |
| D943,092 | S | 2/2022 | Buehrle |
| 11,279,098 | B2 | 3/2022 | Groh |
| 11,285,504 | B2 | 3/2022 | Wilkerson |
| D952,137 | S | 5/2022 | Chandrapati |
| 11,324,660 | B2 | 5/2022 | Geser |
| D954,943 | S | 6/2022 | Byron |
| 11,351,090 | B2 | 6/2022 | Brandenburger |
| 11,351,715 | B2 | 6/2022 | Sauter |
| 11,353,406 | B2 | 6/2022 | Prinz |
| 11,377,263 | B2 | 7/2022 | Gydesen |
| 11,382,833 | B2 | 7/2022 | Koska |
| 11,396,123 | B2 | 7/2022 | Hoshino |
| 11,400,241 | B2 | 8/2022 | Patton |
| 11,400,637 | B2 | 8/2022 | Shiokawa |
| 11,400,638 | B2 | 8/2022 | Hoshino |
| 11,419,984 | B2 | 8/2022 | Schabbach |
| 11,446,209 | B2 | 9/2022 | Barkman |
| 11,446,856 | B2 | 9/2022 | Furlotti |
| 11,534,551 | B2 | 12/2022 | Ferreri |
| 11,565,838 | B2 | 1/2023 | Meier |
| 11,591,126 | B2 | 2/2023 | Köppel |
| 11,607,369 | B2 | 3/2023 | Koska |
| 11,638,783 | B2 | 5/2023 | Consolaro |
| 11,648,180 | B2 | 5/2023 | Genosar |
| D992,110 | S | 7/2023 | Price |
| D1,052,082 | S | 11/2024 | Price |
| 2002/0104856 | A1 | 8/2002 | Clark |
| 2003/0050602 | A1 | 3/2003 | Pettis |
| 2003/0186456 | A1 | 10/2003 | Stroup |
| 2004/0015131 | A1 | 1/2004 | Flaherty |
| 2004/0118477 | A1 | 6/2004 | Desmond |
| 2005/0049560 | A1 | 3/2005 | Hauri |
| 2006/0032189 | A1 | 2/2006 | Giacobbe |
| 2006/0073173 | A1 | 4/2006 | Banach |
| 2006/0108385 | A1 | 5/2006 | Zahn |
| 2007/0167904 | A1 | 7/2007 | Zinger |
| 2007/0191780 | A1 | 8/2007 | Modi |
| 2007/0260188 | A1 | 11/2007 | Kelly |
| 2008/0000798 | A1 | 1/2008 | Gutmann |
| 2008/0083691 | A1 | 4/2008 | Poynter |
| 2008/0228162 | A1* | 9/2008 | Trager ................... A61J 1/067 |
| | | | 604/407 |
| 2008/0243077 | A1 | 10/2008 | Bivin |
| 2008/0258334 | A1 | 10/2008 | Hansen |
| 2008/0262466 | A1 | 10/2008 | Smith |
| 2009/0025823 | A1 | 1/2009 | Hansen |
| 2009/0171311 | A1 | 7/2009 | Genosar |
| 2009/0216212 | A1 | 8/2009 | Fangrow, Jr. |
| 2009/0230077 | A1 | 9/2009 | Poynter |
| 2009/0230080 | A1 | 9/2009 | Hansen |
| 2010/0163577 | A1 | 7/2010 | Hansen |
| 2010/0249716 | A1 | 9/2010 | Wong |
| 2011/0031157 | A1 | 2/2011 | Nakano |
| 2011/0131929 | A1 | 6/2011 | Mcaffer |
| 2011/0135720 | A1 | 6/2011 | Seabrook, Jr. |
| 2011/0160677 | A1 | 6/2011 | March |
| 2011/0186451 | A1 | 8/2011 | Pontus |
| 2011/0224640 | A1 | 9/2011 | Bernd |
| 2012/0027818 | A1 | 2/2012 | Glausch |
| 2012/0074001 | A1 | 3/2012 | Amir |
| 2012/0078215 | A1 | 3/2012 | Finke |
| 2012/0083744 | A1 | 4/2012 | Finke |
| 2012/0179109 | A1 | 7/2012 | Takemoto |
| 2012/0238962 | A1 | 9/2012 | Chin |
| 2013/0015204 | A1 | 1/2013 | Gol |
| 2013/0098864 | A1 | 4/2013 | Fontana |
| 2013/0104324 | A1 | 5/2013 | Greer, Jr. |
| 2013/0110053 | A1 | 5/2013 | Yoshino |
| 2013/0345672 | A1 | 12/2013 | Ferreri |
| 2013/0345673 | A1 | 12/2013 | Ferreri |
| 2014/0008366 | A1 | 1/2014 | Genosar |
| 2014/0039444 | A1 | 2/2014 | Akihito |
| 2014/0046270 | A1 | 2/2014 | Thornton |
| 2014/0054295 | A1 | 2/2014 | Holtwick |
| 2014/0069839 | A1 | 3/2014 | Colin |
| 2014/0188502 | A1 | 7/2014 | Defrank |
| 2014/0224815 | A1 | 8/2014 | Gallem |
| 2014/0231456 | A1 | 8/2014 | Marshall |
| 2014/0291278 | A1 | 10/2014 | Colin |
| 2014/0323975 | A1 | 10/2014 | Thornton |
| 2015/0136622 | A1 | 5/2015 | Genosar |
| 2015/0165123 | A1 | 6/2015 | Thornton |
| 2015/0202372 | A1 | 7/2015 | Ali |
| 2015/0283332 | A1 | 10/2015 | Woehr |
| 2015/0297837 | A1 | 10/2015 | Schraga |
| 2015/0359708 | A1 | 12/2015 | Boomgard |
| 2016/0022541 | A1 | 1/2016 | Dalal |
| 2016/0063215 | A1 | 3/2016 | Zamer |
| 2016/0074586 | A1 | 3/2016 | Mernøe |
| 2016/0120749 | A1 | 5/2016 | Hansen |
| 2016/0144130 | A1 | 5/2016 | Thornton |
| 2016/0151240 | A1 | 6/2016 | Brandenburger |
| 2016/0175544 | A1 | 6/2016 | Koska |
| 2016/0206417 | A1 | 7/2016 | Levine |
| 2016/0246943 | A1 | 8/2016 | Lake |
| 2016/0354537 | A1* | 12/2016 | Jozwik .............. A61M 5/14566 |
| 2017/0007767 | A1 | 1/2017 | Schabbach |
| 2017/0128676 | A1 | 5/2017 | Spallek |
| 2018/0072480 | A1 | 3/2018 | Genosar |
| 2018/0153772 | A1* | 6/2018 | Spallek ................... A61J 1/201 |
| 2018/0193565 | A1 | 7/2018 | Koska |
| 2018/0193571 | A1 | 7/2018 | Koska |
| 2018/0193572 | A1 | 7/2018 | Koska |
| 2018/0197143 | A1 | 7/2018 | Daub |
| 2018/0235839 | A1 | 8/2018 | Johnson |
| 2018/0235840 | A1 | 8/2018 | Genosar |
| 2018/0280234 | A1 | 10/2018 | Brevik-Andersen |
| 2019/0009068 | A1 | 1/2019 | Margoosian |
| 2019/0046402 | A1 | 2/2019 | Desbrosses |
| 2019/0060168 | A1 | 2/2019 | Koska |
| 2019/0060573 | A1 | 2/2019 | Consolaro |
| 2019/0156931 | A1 | 5/2019 | Skoda |
| 2019/0214116 | A1 | 7/2019 | Eberting |
| 2019/0224424 | A1 | 7/2019 | Helmer |
| 2020/0100985 | A1 | 4/2020 | Auerbach |
| 2020/0118164 | A1 | 4/2020 | Defrank |
| 2020/0129698 | A1 | 4/2020 | Chowdhury |

(56) References Cited

U.S. PATENT DOCUMENTS

| | | | |
|---|---|---|---|
| 2020/0164563 A1 | 5/2020 | Spallek | |
| 2020/0172271 A1 | 6/2020 | Colangelo | |
| 2020/0246547 A1* | 8/2020 | Glenting | A61M 5/345 |
| 2020/0276082 A1 | 9/2020 | Koska | |
| 2020/0384186 A1 | 12/2020 | Consolaro | |
| 2021/0030965 A1 | 2/2021 | Koska | |
| 2021/0128835 A1* | 5/2021 | Koska | A61M 5/288 |
| 2021/0244888 A1 | 8/2021 | Ryan | |
| 2021/0353538 A1 | 11/2021 | Humeniuk | |
| 2022/0024616 A1 | 1/2022 | Lema Martinez | |
| 2022/0041317 A1 | 2/2022 | Hammer | |
| 2022/0133695 A1 | 5/2022 | Terraz Mendoza | |
| 2022/0203596 A1 | 6/2022 | Yoshino | |
| 2022/0273923 A1 | 9/2022 | Zeira | |
| 2022/0273924 A1 | 9/2022 | Kamen | |
| 2022/0315296 A1 | 10/2022 | Gamboa Burgos | |
| 2022/0323301 A1 | 10/2022 | Koska | |
| 2022/0336074 A1 | 10/2022 | Bakos | |
| 2022/0336076 A1 | 10/2022 | Albertini | |
| 2022/0371873 A1 | 11/2022 | Hayakawa | |
| 2022/0401300 A1 | 12/2022 | Ikeda | |
| 2022/0409830 A1 | 12/2022 | Shahaf | |
| 2023/0045719 A1 | 2/2023 | Koska | |
| 2023/0064428 A1 | 3/2023 | Price | |
| 2023/0081577 A1 | 3/2023 | Walker et al. | |
| 2023/0087192 A1 | 3/2023 | Ferreri | |
| 2023/0099753 A1 | 3/2023 | Genosar | |
| 2023/0141404 A1 | 5/2023 | Price | |
| 2023/0158255 A1 | 5/2023 | Federico | |
| 2023/0173178 A1 | 6/2023 | Clapham | |
| 2023/0190581 A1 | 6/2023 | Hover | |
| 2023/0192346 A1 | 6/2023 | Bouteloup | |
| 2023/0192367 A1 | 6/2023 | Luigi | |
| 2023/0201387 A1 | 6/2023 | Wendy | |
| 2023/0226276 A1 | 7/2023 | Amiri | |
| 2023/0226743 A1 | 7/2023 | Schnell | |
| 2023/0248897 A1 | 8/2023 | Murray | |
| 2023/0248957 A1 | 8/2023 | Juergen | |
| 2023/0270951 A1 | 8/2023 | Cha | |
| 2024/0009397 A1 | 1/2024 | In | |
| 2024/0009398 A1 | 1/2024 | Koska | |
| 2024/0058217 A1 | 2/2024 | Price | |

FOREIGN PATENT DOCUMENTS

| | | | |
|---|---|---|---|
| CA | 2105031 | | 3/1994 |
| CN | 1196023 A | | 10/1998 |
| CN | 104640594 | | 5/2015 |
| CN | 112829265 A | | 5/2021 |
| CN | 115259051 A | | 11/2022 |
| CN | 217891819 U | | 11/2022 |
| CN | 217894251 U | | 11/2022 |
| CN | 218020077 U | | 12/2022 |
| EP | 0310227 | | 4/1989 |
| EP | 0388360 | | 9/1990 |
| EP | 0685400 | | 12/1995 |
| EP | 0849173 A1 | | 6/1998 |
| EP | 0903180 | | 3/1999 |
| EP | 0930238 A1 | | 7/1999 |
| EP | 1726285 | | 11/2006 |
| EP | 2554201 | | 2/2013 |
| EP | 2554207 | | 2/2013 |
| EP | 2571553 | | 3/2013 |
| EP | 2665502 | | 11/2013 |
| EP | 2919834 | | 9/2015 |
| EP | 3173113 | | 5/2017 |
| EP | 3518860 | | 8/2019 |
| FR | 2990687 A1 | | 11/2013 |
| GB | 2490111 | | 10/2012 |
| GB | 2495741 | | 4/2013 |
| GB | 2495741 A | | 4/2013 |
| IN | 201741030340 | | 1/2019 |
| JP | 2009183909 A | | 8/2009 |
| JP | 2015109883 | | 6/2015 |
| JP | 2019034072 | | 3/2019 |

| | | | |
|---|---|---|---|
| KR | 200345715 | | 3/2004 |
| KR | 100615527 | | 8/2006 |
| RU | 2643432 | | 2/2018 |
| WO | 1989007462 | | 8/1989 |
| WO | 1993017728 | | 9/1993 |
| WO | 1997010156 | | 3/1997 |
| WO | 1998025660 | | 6/1998 |
| WO | 1999043549 | | 9/1999 |
| WO | 0018648 A1 | | 4/2000 |
| WO | 2001043799 | | 6/2001 |
| WO | 2004055143 | | 7/2004 |
| WO | 2007007178 A1 | | 1/2007 |
| WO | 2008086552 | | 7/2008 |
| WO | 2010081174 | | 7/2010 |
| WO | 2011008190 | | 1/2011 |
| WO | 2011026050 | | 3/2011 |
| WO | 2011035503 A1 | | 3/2011 |
| WO | 2011075798 | | 6/2011 |
| WO | 2012011115 | | 1/2012 |
| WO | 2012026551 | | 3/2012 |
| WO | 2012064761 | | 5/2012 |
| WO | 2012099898 | | 7/2012 |
| WO | 2012137945 | | 10/2012 |
| WO | 2012148043 | | 11/2012 |
| WO | 2012156822 | | 11/2012 |
| WO | 2013114357 | | 8/2013 |
| WO | 2013149042 A1 | | 10/2013 |
| WO | 2013162637 A1 | | 10/2013 |
| WO | 2014035935 | | 3/2014 |
| WO | 2014135108 | | 9/2014 |
| WO | 2014135108 A1 | | 9/2014 |
| WO | 2014184121 | | 11/2014 |
| WO | 2014189761 A1 | | 11/2014 |
| WO | 2015036536 | | 3/2015 |
| WO | 2015045740 | | 4/2015 |
| WO | 2015074087 | | 5/2015 |
| WO | 2015134307 | | 9/2015 |
| WO | 2015145902 | | 10/2015 |
| WO | 2015187518 | | 12/2015 |
| WO | 2015200261 A1 | | 12/2015 |
| WO | 2016032814 | | 3/2016 |
| WO | 2016097872 | | 6/2016 |
| WO | 2017001918 | | 1/2017 |
| WO | 2017001919 | | 1/2017 |
| WO | 2017001921 | | 1/2017 |
| WO | 2017001922 | | 1/2017 |
| WO | 2017001923 | | 1/2017 |
| WO | 2017001925 | | 1/2017 |
| WO | 2017103954 A1 | | 6/2017 |
| WO | 2017125859 | | 7/2017 |
| WO | 2017187262 | | 11/2017 |
| WO | 2017187262 A1 | | 11/2017 |
| WO | 2018002113 | | 1/2018 |
| WO | 2018028820 | | 2/2018 |
| WO | 2019040575 A1 | | 2/2019 |
| WO | 2019099954 | | 5/2019 |
| WO | 2019108577 A1 | | 6/2019 |
| WO | 2019154600 | | 8/2019 |
| WO | 2019164478 | | 8/2019 |
| WO | 2019246435 | | 12/2019 |
| WO | 2020055960 A1 | | 3/2020 |
| WO | 2021059213 | | 4/2021 |
| WO | 2021079404 | | 4/2021 |
| WO | 2021186485 | | 9/2021 |
| WO | 2021186485 A1 | | 9/2021 |
| WO | 2021207040 | | 10/2021 |
| WO | 2021226564 | | 11/2021 |
| WO | 2022002863 | | 1/2022 |
| WO | 2022005310 | | 1/2022 |
| WO | 2022026275 | | 2/2022 |
| WO | 2022053948 | | 3/2022 |
| WO | 2022091003 | | 5/2022 |
| WO | 2022112543 | | 6/2022 |
| WO | 2022117361 | | 6/2022 |
| WO | 2022120269 | | 6/2022 |
| WO | 2022133283 | | 6/2022 |
| WO | 2022135945 | | 6/2022 |
| WO | 2022115598 | | 8/2022 |
| WO | 2022180376 | | 9/2022 |

(56)         References Cited

FOREIGN PATENT DOCUMENTS

| WO | 2022180488 | 9/2022 |
|----|------------|--------|
| WO | 2022185350 | 9/2022 |
| WO | 2022186886 | 9/2022 |
| WO | 2022186888 | 9/2022 |
| WO | 2022204408 | 9/2022 |
| WO | 2022207136 | 10/2022 |
| WO | 2022208318 | 10/2022 |
| WO | 2022208488 | 10/2022 |
| WO | 2022256834 | 12/2022 |
| WO | 2022268253 | 12/2022 |
| WO | 2022269651 | 12/2022 |
| WO | 2023281194 | 1/2023 |
| WO | 2023018840 | 2/2023 |
| WO | 23045589 | 3/2023 |
| WO | 23045590 | 3/2023 |
| WO | 23049213 | 3/2023 |
| WO | 2023039126 | 3/2023 |
| WO | 2023045589 A1 | 3/2023 |
| WO | 2023045590 A1 | 3/2023 |
| WO | 2023049213 | 3/2023 |
| WO | 2023086515 A1 | 5/2023 |
| WO | 2023091358 | 5/2023 |
| WO | 2023102008 | 6/2023 |
| WO | 2023104995 | 6/2023 |
| WO | 2023122619 | 6/2023 |
| WO | 2023147491 | 8/2023 |
| WO | 2023244561 | 12/2023 |
| WO | 2024163988 | 8/2024 |

OTHER PUBLICATIONS

Office Action for Indian Application 201827038286 dated Aug. 6, 2021; 6 pps.
Office Action for Indian Application 201827038286 dated Jul. 2, 2021; 8 pps.
Office Action for Korean Patent Application No. 10-2018-7030866 dated Mar. 30, 2022; 4 pps.
Office Action for Korean Patent Application No. 10-2018-7030866 dated Sep. 24, 2021; 17 pps.
Office Action for Mexican Application MX/a/2018/000257 dated Mar. 2, 2022; 5 pps.
Office Action for Mexican Application MX/a/2018/000258 dated Jul. 6, 2022; 3 pps.
Office Action for Mexican Application MX/a/2018/000258 dated Jul. 18, 2022; 5 pps.
Search Report for European Application 18877931.8 dated Jul. 7, 2021; 9 pps.
Search Report for European Application 18877931.8 dated Oct. 19, 2021; 10 pps.
Supplemental European Search Report for European Application No. 19823345.4 dated Feb. 7, 2022; 6 pps.
Syrette "https://en.wikipedia.org/wiki/Syrette" download date: Apr. 23, 2020; 2 pps.
Written Opinion for Application PCT/IB2021/058168 dated Nov. 11, 2021; 9 pps.
Written Opinion for Application PCT/IB2021/059993 dated Nov. 22, 2021; 10 pps.
Written Opinion for Application PCT/US2021/025683 dated Jul. 8, 2021; 4 pps.
Written Opinion for Application PCT/US21/042671 dated Nov. 5, 2021; 9 pps.
Written Opinion for Application PCT/US21/31452 dated Sep. 1, 2021; 15 pps.
Written Opinion for Application PCT/US21/61991 dated Feb. 16, 2022; 9 pps.
Written Opinion for Application PCT/US22/44291 dated Dec. 22, 2022; 5 pps.
Written Opinion for PCT/IB2016/001026 dated Nov. 7, 2016; 5 pps.
Written Opinion for PCT/IB2016/001027 dated Nov. 2, 2016; 5 pps.
Written Opinion for PCT/IB2016/001033 dated Dec. 7, 2016; 6 pps.

Written Opinion for PCT/IB2016/001050 dated Nov. 14, 2016; 5 pps.
Written Opinion for PCT/IB2021/058168 dated Nov. 22, 2021; 9 pps.
Written Opinion for PCT/IB216/001042 dated Dec. 20, 2016; 6 pps.
Written Opinion for PCT/IIB2016/001034 dated Dec. 9, 2016; 6 pps.
Written Opinion for PCT/US21/064155 dated Mar. 21, 2022; 3 pps.
Written Opinion for PCT/US22/40006 dated Nov. 7, 2022; 6 pps.
Written Opinion for WO 2016097872 dated May 9, 2016; 2 pps.
Written Opinion for WO2017/187262 dated Sep. 4, 2017; 7 pps.
Written Opinion or PCT/US18/61696 dated Mar. 7, 2019; 3 pps.
Written Opinion or PCT/US2019/038302 dated Dec. 19, 2019; 4pps.
Australian Application 2022203652 dated Oct. 20, 2023; 7 pps.
Final Office Action dated Dec. 21, 2023 for U.S. Appl. No. 17/849,780; 13 pgs.
Final Office Action for U.S. Appl. No. 15/741,012 dated Oct. 2, 2019; 7 pps.
Final Office Action for U.S. Appl. No. 14/575,635 dated Dec. 14, 2017; 16 pps.
Final Office Action for U.S. Appl. No. 16/876,417 dated Dec. 28, 2022; 6 pps.
International Search Report for PCT Application No. PCT/US21/064155 dated Mar. 21, 2022; 2 pps.
International Search Report for PCT/IB2015/002531 dated Jan. 5, 2017; 3 pps.
International Search Report for PCT/IB2016/001026 dated Jan. 5, 2017; 4 pps.
International Search Report for PCT/IB2016/001027 dated Jan. 5, 2017; 3 pps.
International Search Report for PCT/US23/25123 dated Sep. 29, 2023; 2 pps.
International Written Opinion for PCT Application No. PCT/US21/064155 dated Mar. 21, 2022; 3 pps.
Notice of Allowance for U.S. Appl. No. 17/072,498 dated Jun. 30, 2023; 7 pgs.
Notice of Allowance dated Jun. 30, 2023 for U.S. Appl. No. 17/072,498 (pp. 1-7).
Notice of Allowance for U.S. Appl. No. 15/741,012 dated Jul. 10, 2020; 7 pps.
Notice of Allowance for U.S. Appl. No. 16/876,417 dated Feb. 2, 2023; 5 pps.
Notice of Hearing for Indian Application 201827038286 dated Jan. 17, 2024; 2 pps.
Office Action (Final Rejection) dated Dec. 21, 2023 for U.S. Appl. No. 17/849,780 (pp. 1-13).
Office Action (Non-Final Rejection) dated Feb. 7, 2023 for U.S. Appl. No. 17/072,498 (pp. 1-9).
Office Action (Non-Final Rejection) dated Aug. 8, 2023 for U.S. Appl. No. 17/849,780 (pp. 1-15).
Office Action (Notice of Allowance and Fees Due (PTOL-85)) dated Jun. 30, 2023 for U.S. Appl. No. 17/072,498 (pp. 1-7).
Office Action for Australian Application 2022203652 dated Jun. 23, 2023; 5 pps.
Office Action for Australian Application 2022203652 dated Oct. 20, 2023; 7 pps.
Office Action for Canadian Application 3021989 dated May 18, 2023; 3 pps.
Office Action for Chinese Application 201880087016.7 dated Jun. 15, 2022; 10 pps.
Office Action for European Patent Application 18877931.8 dated May 23, 2023; 4 pps.
Office Action for Indian Patent Application 201827038286 dated Jun. 8, 2021; 6 pps.
Office Action for Indian Patent Application 202027021653 dated May 6, 2022; 5 pps.
Office Action for Korean Patent Application 10-2018-7003178 dated Feb. 20, 2023; 2 pps.
Office Action for Korean Patent Application 10-2020-7017317 dated Aug. 1, 2023; 2 pps.
Office Action for Mexican Patent Application MX/a/2017/008000 dated Apr. 26, 2022; 6 pps.

(56)             References Cited

OTHER PUBLICATIONS

Office Action for Mexican Patent Application MX/a/2018/000257 dated Mar. 2, 2022; 4 pps.
Office Action for Mexican Patent Application MX/a/2018/012967 dated Nov. 1, 2022; 3 pps.
Office Action for U.S. Appl. No. 14/575,635 dated Mar. 3, 2017; 25 pps.
Office Action for U.S. Appl. No. 14/575,635 dated Oct. 9, 2018; 16 pps.
Office Action for U.S. Appl. No. 15/741,011 dated Oct. 2, 2019; 7 pps.
Office Action for U.S. Appl. No. 17/072,498 dated Feb. 7, 2023; 9 pps.
Written Opinion for PCT/US23/25123 dated Sep. 29, 2023; 9 pps.
Written Opinion for PCT/IB2015/002531 dated Jun. 23, 2016; 6 pps.
Written Opinion for PCT/IB2016/001026 dated Jan. 5, 2017; 5 pps.
Written Opinion for PCT/IB2016/001027 dated Jan. 5, 2017; 5 pps.
Bufus Plastic Drop https://www.alamy.com/stock-photo-bufus-plastic-drop-ampoule-vial-spray-the-medicine-cast-resin-sealed 131358830.html Nov. 10, 2015 (Year: 2015).
International Search Report for Application PCT/US2022/49608 dated Feb. 21, 2023; 3 pps.
Notice of Allowance dated Mar. 21, 2023 for U.S. Appl. No. 29/803,121 (pp. 1-9).
Notice of Allowance dated May 5, 2023 for U.S. Appl. No. 29/803,121 (pp. 1-2).
Office Action (Notice of Allowance and Fees Due (PTOL-85)) dated Feb. 2, 2023 for U.S. Appl. No. 16/876,417 (pp. 1-5).
Woodstock Sterile Solutions https://woodstocksterilesolutions.com/manufacturing-capability/ Date Accessed Mar. 3, 2023 (Year: 2023).
Written Opinion for Application PCT/US2022/49608 dated Feb. 16, 2023; 6 pps.
Extended European Search Report (EESR) for European Patent Application No. 21907935.7 mailed on Sep. 23, 2024 (7 pages).
International Search Report for PCT/US24/14394 dated Jul. 29, 2024; 6 pps.
Notice of Allowance dated Jul. 17, 2024 for U.S. Appl. No. 29/736,603; 8 pgs.
Notice of Allowance/Intention to Grant for Canadian Patent Application No. 3,021,989 mailed on Oct. 15, 2024 (1 page).
Office Action (Non-Final Rejection; dated Apr. 23, 2024 for U.S. Appl. No. 17/129,593 (pp. 1-20).
Office Action (Non-Final Rejection) dated Aug. 28, 2024 for U.S. Appl. No. 18/181,664 (pp. 1-6).
Office Action (Notice of Allowance and Fees Due (PTOL-85)) dated Apr. 24, 2024 for U.S. Appl. No. 17/849,780; 7 pgs.
Office Action (Notice of Allowance and Fees Due (PTOL-85)) dated May 23, 2024 for U.S. Appl. No. 17/849,780; 3 pgs.
Office Action (Notice of Allowance and Fees Due (PTOL-85)) dated Jul. 15, 2024 for U.S. Appl. No. 17/849,780, 3 pgs.
Office Action for U.S. Appl. No. 18/181,664 dated Aug. 28, 2024; 6 pps.
Refresh Classic Lubricant Eye Drops, first available May 21, 2007, amazon.com, [online], [site visited Jul. 8, 2024], Available from internet URL: https://www.amazon.com/dp/B000R2VCIA (Year: 2007).
Written Opinion for PCT/US24/14394 dated Jul. 29, 2024; 10 pps.
Allowance Notification for Chinese Application 201680050853.3 dated Jun. 8, 2021; 1 pp.
Allowance Notification for Chinese Application 201780025582.0 dated Jun. 21, 2021; 1 pp.
Communication prusuant to Article 94(3) EPC for EP 17730256.9 dated Aug. 31, 2022; 5 pps.
Examination Report for PCT/IB2015/002531 dated May 28, 2020; 5 pps.
International Preliminary Report on Patentability for PCT/US18/61696 dated May 28, 2020; 4pps.
International Search Report for Application PCT/IB2016/001033 dated Dec. 9, 2016; 4 pps.

International Search Report for Application PCT/IB2016/001034 dated Dec. 13, 2016; 3 pps.
International Search Report for Application PCT/IB2016/001042 dated Dec. 22, 2016; 3 pps.
International Search Report for Application PCT/IB2021/058168 dated Nov. 11, 2021; 6 pps.
International Search Report for Application PCT/IB2021/058168 dated Nov. 22, 2021; 6 pps.
International Search Report for Application PCT/IB2021/059993 dated Nov. 22, 2021; 8 pps.
International Search Report for Application PCT/US2021/025683dated Jul. 8, 2021; 2 pps.
International Search Report for Application PCT/US21/042671 dated Nov. 5, 2021; 2 pps.
International Search Report for Application PCT/US21/064155 dated Mar. 21, 2022; 2 pps.
International Search Report for Application PCT/US21/31452 dated Sep. 1, 2021; 2 pps.
International Search Report for Application PCT/US21/61991 dated Feb. 16, 2022; 2 pps.
International Search Report for Application PCT/US22/40006 dated Nov. 7, 2022; 5 pps.
International Search Report for Application PCT/US22/44291 dated Dec. 22, 2022; 5 pps.
International Search Report for PCT/IB2016/001027 dated Jan. 5, 2017; 2 pps.
International Search Report for PCT/IB2016/001050 dated Nov. 15, 2016; 2 Pps.
International Search Report for PCT/US18/61696 dated Mar. 7, 2019; 2 pps.
International Search Report for PCT/US2019/038302 dated Dec. 19, 2019; 2pps.
International Search Report for WO 2016097872 dated May 9, 2016, 1 pps.
International Search Report for WO2017/187262 dated Sep. 4, 2017; 3 pps.
International Search Report or PCT/IB2016/001026 dated Nov. 8, 2016; 3 pps.
Notice of Acceptance for Australian Application 2017256152 dated Apr. 11, 2022; 3 pps.
Notice of Grant for 16774977.9 dated Mar. 12, 2020; 2 pps.
Office Action (Final Rejection) dated Dec. 28, 2022 for U.S. Appl. No. 16/876,417 (pp. 1-6).
Office Action (Final) for U.S. Appl. No. 14/575,635 dated Dec. 14, 2017; 44 pps.
Office Action (Non-Final Rejection) dated Jan. 12, 2022 for U.S. Appl. No. 16/169,983 (pp. 1-12).
Office Action (Non-Final Rejection) dated Jun. 8, 2022 for U.S. Appl. No. 16/876,417 (pp. 1-9).
Office Action (Non-final) for U.S. Appl. No. 14/575,635 dated Mar. 23, 2017; 44 pps.
Office Action (Non-final) for U.S. Appl. No. 14/575,635 dated Oct. 9, 2018; 39 pps.
Office Action (Non-final) for U.S. Appl. No. 15/741,009 dated Oct. 2, 2019; 6 pps.
Office Action (Non-final) for U.S. Appl. No. 15/741,011 dated Oct. 2, 2019; 8 pps.
Office Action (Notice of Allowance and Fees Due (PTOL-85)) dated Feb. 23, 2022 for U.S. Appl. No. 16/169,983 (pp. 1-7).
Office Action (Notice of Allowance and Fees Due (PTOL-85)) dated May 17, 2022 for U.S. Appl. No. 16/169,983 (pp. 1-7).
Office Action (Notice of Allowance and Fees Due (PTOL-85)) dated Jun. 2, 2022 for U.S. Appl. No. 16/169,983 (pp. 1-3).
Office Action (Notice of Allowance and Fees Due (PTOL-85)) dated Jul. 10, 2020 for U.S. Appl. No. 15/741,012 (pp. 1-6).
Office Action (Notice of Allowance and Fees Due (PTOL-85)) dated May 17, 2022 for U.S. Appl. No. 16/169,983; 7 pps.
Office Action for U.S. Appl. No. 15/741,009 dated Oct. 2, 2019; 6 pps.
Office Action for U.S. Appl. No. 15/741,011 dated Oct. 2, 2019; 8pps.
Office Action for U.S. Appl. No. 15/741,012 dated Oct. 2, 2019; 7pps.

(56)                    References Cited

OTHER PUBLICATIONS

Office Action for U.S. Appl. No. 16/876,417 dated Jun. 8, 2022; 9 pps.

Office Action for Australian Application 2017256152 dated Jul. 29, 2021; 6 pps.

Office Action for Australian Application 2017256152 dated Nov. 12, 2021; 4 pps.

Office Action for Chinese Application 201680050853.3 dated Mar. 18, 2020; 3 pps.

Office Action for Chinese Application 201680050853.3 dated Nov. 27, 2020; 3 pps.

Office Action for Chinese Application 201780025582.0 dated Oct. 30, 2020; 2 pps.

Office Action for Chinese Application 201880087016.7 dated Feb. 24, 2022; 7 pps.

Communication pursuant to Article 94(3) EPC (Office Action) for EP 17730256.9 dated Jan. 23, 2025 (7 pgs.).

Communication pursuant to Article 94(3) EPC (Office Action) for EP 17730256.9 dated Oct. 16, 2025 (7 pgs.).

Communication pursuant to Rules 161(1) and 162 EPC for European Patent Application No. 22830002.6 mailed on Jun. 18, 2024 (3 pages).

Communication pursuant to Rules 161(1) and 162 EPC for European Patent Application No. 24712355.7 mailed on Sep. 16, 2025 (3 pages).

Communication pursuant to Rules 70(2) and 70a(2) EPC for European Patent Application No. 21907935.7 mailed on Oct. 11, 2024 (1 page).

Communication pursuant to Rules 70(2) and 70a(2) EPC for European Patent Application No. 23824485.9 mailed on Sep. 9, 2025 (1 page).

Extended European Search Report (EESR) for European Patent Application No. 23824485.9 mailed on Aug. 22, 2025 (9 pages).

Final Office Action for U.S. Appl. No. 17/129,593 mailed on Feb. 26, 2025 (35 pages).

Notice of Allowance for U.S. Appl. No. 29/966,986 dated Oct. 23, 2025 (pp. 1-7).

Notice of Allowance for U.S. Appl. No. 17/129,593 mailed on Oct. 16, 2025 (11 pages).

Notice of Allowance for U.S. Appl. No. 18/181,664 mailed on Feb. 20, 2025 (7 pgs.).

Notice of Allowance/Intention to Grant for Indian Patent Application 201827038286 dated Jul. 11, 2023 (1 pg).

Notice of Allowance/Intention to Grant for Indian Patent Application 202027021653 dated Feb. 7, 2024 (1 pg).

Notice of Allowance/Intention to Grant for Korean Patent Application 10-2018-7030866 dated Nov. 9, 2022 (3 pgs).

Notice of Allowance/Intention to Grant for Korean Patent Application 10-2020-7017317 dated Aug. 1, 2023 (2 pps).

Notice of Allowance/Intention to Grant for Mexican Patent Application MX/a/2018/012967 dated May 16, 2023 (2 pgs).

Oasis Tears Plus Preservative-Free Lubricant Eye Drops, 30 containers, first available Dec. 29, 2011, 4 pages, amazon.com, [ online], [site visited Sep. 27, 2025], Available from internet URL: https://www.amazon.com/ Oasis-TEARS-Preservative-Free-Lubricant-containers/dp/B006R62UZO/(Year 2011).

Office Action (Non-Final Rejection) dated Jan. 12, 2026 for U.S. Appl. No. 18/267,365 (pp. 1-14).

Office Action (Non-Final Rejection) dated Jul. 2, 2025 for U.S. Appl. No. 17/960,111; 11 pgs.

Office Action (Notice of Allowance and Fees Due (PTOL-85)) dated Feb. 20, 2025 for U.S. Appl. No. 18/181,664; 7 pgs.

Office Action (Notice of Allowance and Fees Due (PTOL-85)) dated Oct. 16, 2025 for U.S. Appl. No. 17/129,593 (pp. 1-11).

Office Action (Notice of Allowance and Fees Due (PTOL-85)) dated Nov. 17, 2025 for U.S. Appl. No. 17/129,593 (pp. 1-2).

Office Action (Restriction Requirement) for U.S. Appl. No. 18/267,365 mailed on Nov. 12, 2025 (6 pages).

Office Action for U.S. Appl. No. 17/960,111 dated Jul. 2, 2025; 11 pps.

Refresh Optive Mega-3 Lubricant Eye Drops, first available Aug. 21, 2017, 6 pages, amazon.com, [online], [site visited Sep. 27, 2025], Available from internet URL: https://www.amazon.com/ Refresh-Optive-Lubricant-Single-Use-Containers/dp/B074ZHK96H/? t=1- Year: 2017).

Summons to Attend Oral Proceedings (Rule 115(1) EPC) for European Patent Application 18877931.8 dated May 23, 2025; 7 pgs.

Office Action (Non-Final Rejection) dated Mar. 23, 2026 for U.S. Appl. No. 17/960,111; pp. 1-13.

Office Action (First Examination Report (FER)) for Indian Patent Application No. 202417038144 mailed on Mar. 16, 2026 (8 pages).

Office Action (First Examination Report (FER)) for Indian Patent Application No. 202417100381 mailed on May 27, 2026 (8 pages).

Office Action (summarized translation) for Chinese Patent Application No. 202180088007.1 mailed on May 7, 2026 (4 pages).

* cited by examiner

766

760

760-1

730

700

710

BFS INJECTION AND CONNECTION ASSEMBLIES

CROSS-REFERENCE TO RELATED APPLICATIONS

The present application claims benefit and priority to, and is a Continuation of: (i) International Patent Application No. PCT/US22/49608 filed on Nov. 10, 2022 and titled "BFS INJECTION AND CONNECTION ASSEMBLIES", which itself claims benefit and priority to and is a non-provisional of (ii) U.S. Provisional Patent Application No. 63/278,469 filed on Nov. 11, 2021 and titled "BFS CONNECTION ASSEMBLIES" and (iii) U.S. Provisional Patent Application No. 63/400,898 filed on Aug. 25, 2022 and titled "BFS CONNECTION ASSEMBLIES", the contents of each of which are hereby incorporated by reference herein.

BACKGROUND

Applicant has previously developed various single-use, single-dose, pre-filled and/or disposable medical injection devices and systems, such as ones utilizing a fluid container manufactured in accordance with a Blow-Fill-Seal (BFS) manufacturing process and mated to one or more components comprising an administration member for injecting a fluid (e.g., a pharmacological agent) from the BFS container into a patient. Applicant's U.S. patent application Ser. No. 17/849,780 titled SYSTEMS AND METHODS FOR FLUID DELIVERY is one example of some embodiments of such injection devices and systems. Such injection devices and systems may benefit from an ability to couple to a wider variety of medical devices, but configuring BFS vials for such connections has proven difficult due to the manufacturing limitations inherent in BFS manufacturing processes. In the case of small form factor BFS vials/bottles, the ability to deliver the entirety of the single-dose stored in the BFS vial may also be of concern due to the nature of the couplings.

SUMMARY

In some embodiments, a BFS connection assembly may comprise a connection element or system formed and configured to mate with and pierce a BFS bottle such that the contents of the BFS bottle may be transferred to a different medical device or system. BFS connection and/or administration assemblies may comprise, for example, (i) a BFS port formed at a first assembly end, the BFS port comprising a seat configured to accept a mounting feature of a BFS bottle inserted into the BFS port; (ii) an outlet port formed at a second assembly end, the outlet port comprising threads; (iii) a projection extending axially from a first projection end at an interior extent of the outlet port, the projection defining a fluid outlet at a second projection end thereof; and/or (iv) a tubular piercing element coupled within the projection and connecting the fluid outlet to the BFS port, wherein the tubular piercing element is disposed to pierce a fluid seal of the BFS bottle in the case that the BFS bottle is inserted into the BFS port and the mounting feature of the BFS bottle is engaged with the seat. According to some embodiments, the projection may comprise a cone. In some embodiments, the cone may be tapered from the first projection end to the second projection end. In some embodiments, the threads of the outlet port may comprise interior threads formed within the outlet port and/or exterior threads formed on an outside surface of the outlet port. According to some embodiments, the tubular piercing element may comprise a metal tube disposed in an interior channel of the projection and a proximate end of the metal tube is beveled to form a point that extends axially into the BFS port. In some embodiments, the seat may comprise an axial track and/or the mounting feature of the BFS bottle may comprise an axial exterior flange.

According to some embodiments, a BFS injection system may comprise a dual-ended BFS bottle in which each end is differently configured for fluid transfer/injection. One end of the BFS bottle may be molded with an integral grip portion and tear line, for example, in which shear force applied via the grip portion may separate the grip portion from the BFS vial, thereby opening the end of the BFS vial and providing access to the fluid stored therein. In some embodiments, the opposite end of the BFS bottle may instead be configured with a puncture surface that requires a puncture element to pierce the seal (e.g., axially) to gain access to the fluid within the BFS bottle. In some embodiments, either end of the BFS bottle may be coupled to various medical delivery devices and/or systems. The BFS bottle may comprise, for example, (i) a compressible fluid reservoir; (ii) a first neck portion in fluid communication with the compressible fluid reservoir and formed at a first end of the BFS bottle; (iii) a second neck portion in fluid communication with the compressible fluid reservoir and formed at a second end of the BFS bottle; (iv) an angled exterior flange formed on an exterior of the first neck portion; (v) a first fluid seal formed at the first end of the BFS bottle, the first fluid seal comprising a grip portion and defining a tear line between the grip portion and the first neck portion; (vi) a mounting feature formed proximate to the second end; and/or (vii) a second fluid seal formed at the second end. In some embodiments, the BFS injection system may comprise the BFS bottle and a BFS connection assembly that permits direct patient injection (e.g., of a single dose of medicament) via the BFS bottle. The BFS injection system may comprise, for example, a needle hub defining a first hub end and a second hub end, the first hub end defining a mounting socket comprising interior threads into which, in the case that the first fluid seal is separated from the BFS bottle at the tear line, the angled exterior flange is axially and rotationally mated, and the second hub end being coupled to a needle such that an application of radially inward force to the compressible fluid reservoir expels a dose of fluid stored in the compressible fluid reservoir through the needle. According to some embodiments, the angled exterior flange may comprise two angled exterior flanges disposed on opposite sides of the first neck portion and each of the two angled exterior flanges extends between one quarter and one third along an outer circumference of the first neck portion. According to some embodiments, first neck portion may define a first exterior diameter at the angled exterior flange and may define a second exterior diameter between the angled exterior flange and the compressible fluid reservoir, and the second exterior diameter may be less than the first exterior diameter. In some embodiments, the first neck portion may comprise, at the second exterior diameter, an axial rib connecting the compressible fluid reservoir to the first neck portion, where the axial rib extends radially outward from the second exterior diameter to the first exterior diameter.

In some embodiments, the BFS injection system may comprise the BFS bottle and a BFS connection assembly that permits the stored fluid to be delivered external to the BFS bottle. The BFS connection assembly may comprise, for example, (i) a BFS port formed at a first assembly end, the BFS port comprising a seat configured to accept the mounting feature of the BFS bottle in the case that the second end of the BFS bottle is inserted into the BFS port; (ii) an outlet port formed at a second assembly end, the outlet port comprising threads; (iii) a projection extending axially from a first projection end at an interior extent of the outlet port, the projection defining a fluid outlet at a second projection end thereof; and/or (iv) a tubular piercing element coupled within the projection and connecting the fluid outlet to the BFS port, wherein the tubular piercing element is disposed to pierce the second fluid seal of the BFS vial in the case that the second end of the BFS bottle is inserted into the BFS port. In some embodiments, the projection may comprise a cone and the cone may be tapered from the first projection end to the second projection end. According to some embodiments, the threads of the outlet port may comprise interior threads formed within the outlet port and/or exterior threads formed on an outside surface of the outlet port. In some embodiments, the tubular piercing element may comprise a metal tube disposed in an interior channel of the projection and a proximate end of the metal tube is beveled to form a point that extends axially into the BFS port. In some embodiments, the seat may comprise an axial track and/or the mounting feature of the BFS bottle may comprise an axial exterior flange.

BRIEF DESCRIPTION OF THE DRAWINGS

An understanding of embodiments described herein and many of the attendant advantages thereof may be readily obtained by reference to the following detailed description when considered with the accompanying drawings, wherein.

DETAILED DESCRIPTION

I. Introduction

Embodiments of the present invention(s) provide systems and methods for pre-filled medical delivery assemblies that overcome drawbacks of current delivery devices and methods. For example, the pre-filled medical delivery assemblies of some embodiments may include a Blow-Fill-Seal (BFS) vial or bottle coupled to one or more specialized collars, assemblies, and/or connectors that facilitate coupling of an administration member (e.g., a needle) to the BFS vial and/or that facilitate transfer of the fluid stored in the BFS bottle to one or more other medical devices and/or systems (e.g., syringes, IntraVenus (IV) fluid bags, etc.). Utilization of such systems that employ BFS bottles and specialized connection assemblies described herein may be advantageous and may address various shortcomings of previous systems.

BFS vials may, for example, offer a less expensive alternative to typical vials or devices created via other manufacturing techniques such as glass or injection-molded plastics. In some embodiments, BFS vials (e.g., due to the nature of the BFS manufacturing process) may not require separate sterilization (e.g., an may accordingly be compatible with a wider array of fluids), may provide enhanced production rates of sterile/aseptic units per hour, and/or may be provided to an end-user for significantly lower per dose/unit costs. In some embodiments, these advantages may come with an attendant drawbacks of reduced manufacturing tolerances and other disadvantages of utilizing a "soft" plastic (e.g., having a Shore/Durometer "D" hardness of between 60 and 70). BFS processes may, for example, offer less precise manufacturing tolerances in the range of five hundredths of an inch (0.05-in; 1.27 mm) to fifteen hundredths of an inch (0.15-in; 3.81 mm)—for linear dimensions, e.g., in accordance with the standard ISO 2768-1 "General tolerances for linear and angular dimensions without individual tolerance indications" published by the International Organization for Standardization (ISO) of Geneva, Switzerland (Nov. 15, 1989) and/or may not be readily adaptable to form certain mating features such as standardized threads. In some embodiments, these drawbacks and/or the deficiencies of prior systems may be advantageously addressed by specific features, configurations, and/or components as described hereinafter.

II. BFS Bottles

Figure 1B:
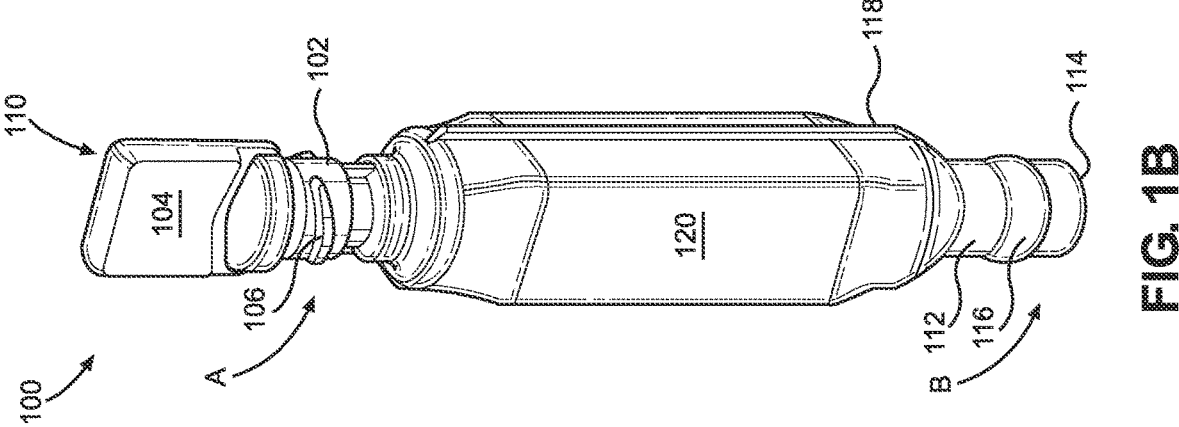
FIG. 1A and FIG. 1B are left front perspective views of a dual-ended BFS bottle system according to some embodiments.
Figure 1A:
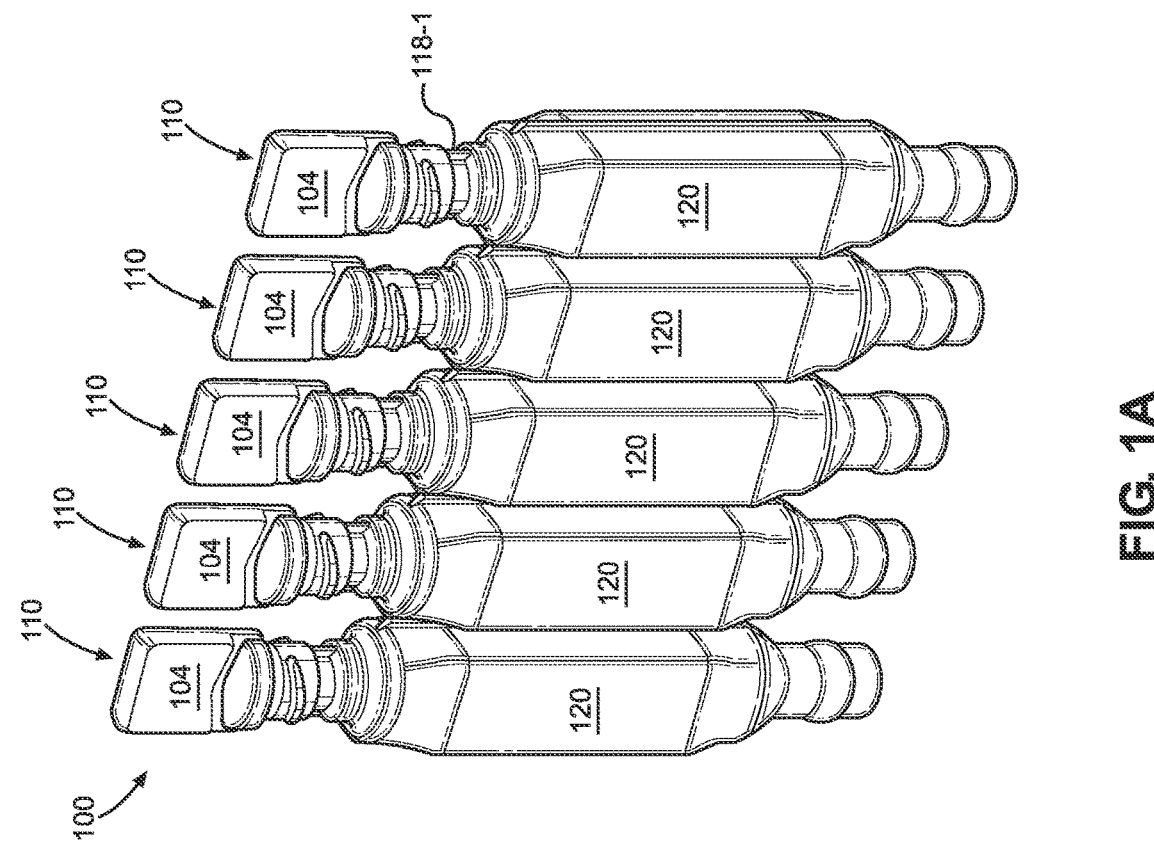

Referring initially to FIG. 1A and FIG. 1B, left front perspective views of a dual-ended BFS vial system 100 according to some embodiments are shown. In some embodiments, the dual-ended BFS vial system 100 may comprise one or more BFS bottles 110 (e.g., dual-ended, as shown) formed or joined together (as depicted in FIG. 1A) or separated (as depicted in FIG. 1B). According to some embodiments, any or all of the dual-ended BFS bottles 110 may comprise and/or define various features and/or components such as a first end "A" and a second end "B". In some embodiments, the first end "A" may comprise and/or define a first neck 102, a first fluid seal 104, and/or a first mounting flange 106. According to some embodiments, the second end "B" may comprise and/or define a second neck 112, a second fluid seal 114, and/or a second mounting flange 116. In some embodiments, each of the BFS bottles 110 may comprise and/or define a reservoir 120 (e.g., a collapsible volume) disposed between the first end "A" and the second end "B" that is in fluid communication with the necks 102, 112.

In some embodiments, the reservoir 120 may be filled (fully or partially) with a fluid or other agent (not separately shown) to be delivered, e.g., to a patient (not shown). According to some embodiments, the fluid may be injected into the BFS bottles 110 in a sterile environment during manufacture via a BFS process and sealed within the BFS bottles 110 via the fluid seals 104, 114. The fluid seals 104, 114 may comprise portions of the molded BFS bottles 110 for example that are (i) configured to be torn, twisted, sheared, broken, and/or ripped away to expel the fluid, e.g., such as by providing a twist, grip portion, and/or pull tab and/or one or more integrated shear or tear lines (e.g., the first fluid seal 104) and/or (ii) configured to be pierced to expel the fluid, e.g., such as by providing a flat or planar piercing surface and/or by being oriented normal to an axis of the BFS bottle 110 (e.g., the second fluid seal 114). In some embodiments, the fluid seals 104, 114 may comprise foil, wax, paper, and/or other thin, frangible and/or pierceable objects or layers coupled to the BFS bottles 110. In some embodiments, the necks 102, 112 of the BFS bottles 110 may comprise the mounting flanges 106, 116 such as, e.g., (i) the angled exterior flange protrusions depicted with respect to the first mounting flange 106 and/or (ii) the "doughnut"-shaped exterior flange depicted with respect to the second mounting flange 116.

According to some embodiments, one or more of the mounting flanges 106, 116 may comprise, work cooperatively with, and/or be functionally replaced by one or more side flanges 118. Two (2) side flanges 118 may be formed on each BFS bottle 110 due to the molding process, for example, and may represent the location of a fused/welded seam between two plastic sheets (parison) that are utilized to form each set (e.g., a "card") of BFS bottles 110. In some embodiments, the first mounting flange 106 may comprise a pair of angled exterior flanges, such as two (2) angled exterior flanges disposed on opposite sides of the first neck portion. According to some embodiments, each of the two angled exterior flanges comprising the exemplary first mounting flange 106 may extend between one quarter (¼) and one third (⅓) of an outer circumference of the first neck portion. In some embodiments, the first neck portion may define a first exterior diameter at or around the angled exterior flanges comprising the exemplary first mounting flange 106 and define a second exterior diameter between the angled exterior flanges comprising the exemplary first mounting flange 106 and the compressible fluid reservoir 120. In some embodiments, the second exterior diameter may be less than the first exterior diameter. The first exterior diameter may be configured such that the angled exterior flanges comprising the exemplary first mounting flange 106 are operable to mate with corresponding threads (not shown) of a device such as a Luer lock connector, for example, while the second exterior diameter may be configured to facilitate a seal with another device's cone feature (not shown; e.g., a Luer slip-style cone) being inserted therein. In some embodiments, the BFS bottles 110 may comprise, e.g., at the lesser second exterior diameter, an axial rib 118-1 that connects the compressible fluid reservoir 120 to the first neck 102. The axial rib 118-1 may, for example, extend radially outward from the second exterior diameter to the first exterior diameter, e.g., thereby creating a bridge or web that strengthens the first neck 102 at the portion(s) thereof that comprise the second exterior diameter.

While the BFS bottles 110 are depicted with two ends ("A" and "B") each comprising fluid seals 104, 114, in some embodiments one of the ends may be walled-off or otherwise comprise a non-functional end that is not configured for piercing or breaching. The contents of the reservoir 120 may only be readily accessible, for example, via one of the ends "A" or "B". Similarly, while each end "A" and "B" is depicted for purposes of example as defining a different style of coupling or connection mechanism, both ends may comprise the same style connection mechanism—e.g., both ends "A" and "B" may, in some embodiments, comprise the "doughnut"-style second mounting flange 116 or both ends "A" and "B" may comprise the angled protrusion-style first mounting flange 106.

In some embodiments, fewer or more components 102, 104, 106, 110, 112, 114, 116, 118, 118-1, 120 and/or various configurations of the depicted components 102, 104, 106, 110, 112, 114, 116, 118, 118-1, 120 may be included in the dual-ended BFS vial system 100 without deviating from the scope of embodiments described herein. In some embodiments, the components 102, 104, 106, 110, 112, 114, 116, 118, 118-1, 120 may be similar in configuration and/or functionality to similarly named and/or numbered components as described herein and/or may be utilized to conduct and/or facilitate methods, processes, and/or procedures described herein.

III. BFS Injection Systems

Referring to FIG. 2A, FIG. 2B, FIG. 2C, FIG. 2D, FIG. 2E, FIG. 2F, FIG. 2G, and FIG. 2H, various views of a BFS injection system 200 according to some embodiments are shown. According to some embodiments, the BFS injection system 200 may comprise a BFS bottle 210 comprising and/or defining a neck 202, a first or removable fluid seal 204 and/or an angled exterior flange 206. In some embodiments, the removable seal 204 may be twisted, sheared, ripped, broken, and/or otherwise removed from the neck 202, e.g., at a tear line 204-1 (e.g., a portion of the neck 202 configured with a wall thickness and/or geometry that makes it weaker than other portions and thereby urges separation at the tear line 204-1). Application of a twisting and/or shear force to the removable fluid seal 204 (e.g., at a grip area comprising a flattened ergonomic portion of the removable fluid seal 204 at a first end or extent of the BFS bottle 210) may cause the removable fluid seal 204 to separate from the neck 202, for example, thereby enabling access and/or communication with fluid stored in a reservoir 220 (e.g., compressible) of the BFS bottle 210. In some embodiments, the BFS bottle 210 may comprise and/or define a side or axial flange 218 and/or a neck rib 218-1. Plastic material between adjacently molded BFS bottles 210 may be molded flat and/or may provide a surface that may be punched or cut to separate adjacent BFS bottles 210, for example, thereby forming and/or defining the side flange 218. In some embodiments, the neck rib 218-1 may comprise a flange or web that bridges a decreased diameter portion of the neck 202, e.g., to provide strength thereto. The neck rib 218-1 may, for example, help ensure that forces applied to the removable fluid seal 204 do not undermine the structural integrity of the neck 202 at the decreased diameter portion, and instead permit the tear line 204-1 to be the weakest, thinnest, and/or most structurally deficient portion of the neck 202 such that any failure is most likely to occur along the tear line 204-1.

According to some embodiments, the BFS injection system 200 may comprise an administration (e.g., injection) assembly, module, or component 230 that is manufactured, assembled, and/or provided as a separate unit from the BFS bottle 210. In some embodiments, the administration assembly 230 may comprise a connector or needle hub 240 which itself comprises, is coupled to, and/or defines various features and/or elements. The needle hub 240 and/or the administration assembly 230 may, for example, be maintained as a closed and/or sterile component via a seal (not shown; e.g., a foil, wax, paper, and/or other thin, pierceable, tear-able, and/or removable object or layer coupled to cover an opening of the needle hub 240) that seals an interior volume, BFS port, or mounting socket 240-1 of the needle hub 240, disposed at a first end (e.g., a first hub end) thereof. According to some embodiments, the needle hub 240 may comprise and/or define one or more coupling or mounting features such as internal threads 242 that are configured to accept the angled exterior flange 206 of the BFS bottle 210 in the case that the neck 202 of the BFS bottle 210 is inserted into the needle hub 240 and/or the administration assembly 230. In some embodiments, the needle hub 240 may comprise one or more of a friction cone 244, an exterior flange 246, and/or a fluid channel inlet 248. The friction cone 244 may, for example, comprise a conical protrusion that extends axially from an interior surface of the mounting socket 240-1. In some embodiments, the friction cone 244 may comprise a tapered projection configured in accordance with the ISO 80369-7:2021 "Small-bore connectors for liquids and gases in healthcare applications—Part 7: Connectors for intravascular or hypodermic applications" standard published by the International Organization for Standardization of Geneva, Switzerland (May, 2021). The friction cone 244 may, for example, comprise a tapered conical (or frusto-conical) projection having a length of seven and on half millimeters (7.5-mm), an end width of four millimeters (4-mm), and a side-slope of three percent (3.0%).

According to some embodiments, the friction cone 244 may be inserted into and/or mate with an interior passage (not separately labeled) of the BFS bottle 210 that is formed and/or revealed upon removal of the removable fluid seal 204. In some embodiments, the fluid channel inlet 248 may be disposed and/or formed on a tip or extent of the friction cone 244. According to some embodiments, the needle hub 240 may comprise, couple to and/or house a needle, canula, and/or other administration member 270, and/or a cap 280 (e.g., selectively engaged and/or coupled to the needle hub 240 to shroud, house, and/or protect the administration member 270). The administration member 270 may, for example, be coupled to and/or within the friction cone 244 such that a first or proximal end of the administration member 270 is in fluid communication with the fluid channel inlet 248 and a second or distal end of the administration member 270 extends axially outward from the needle hub 240 (and, e.g., is selectively shrouded by the cap 280 that may be engaged with and/or coupled to the exterior flange 246 of the needle hub 240). According to some embodiments, the BFS injection system 200 may include a modular design consisting of separately constructed components 210, 240, 270, 280 cooperatively arranged and coupled to one another.

In some embodiments, the administration assembly 230 may be manufactured, packaged, shipped, stored, and/or provided as separate components. In such a manner, the administration assembly 230 may not need to be stored or shipped in accordance with often restrictive requirements imposed on medicaments and may accordingly reduce the amount of space required for such specialized storage and/or shipping. The administration assembly 230 may also or alternatively be manufactured, stored, and/or shipped in advance (e.g., at a first time) while the BFS bottle 210 that is pre-filled with the fluid may be manufactured, stored, and/or shipped at a later time (e.g., a second time). In some embodiments, the delay between the first time and the second time may be lengthy without causing determinantal effects, as the administration assembly 230 may be stored, in some embodiments, indefinitely. In such a manner, units of the administration assembly 230 may be provided to be on-hand in advance of the availability and/or arrival of the BFS bottle 210, reducing supply chain constraints in the case of proactive administration assembly 230 procurement.

Figures 2A, 2B, 2C, 2D, 2E:
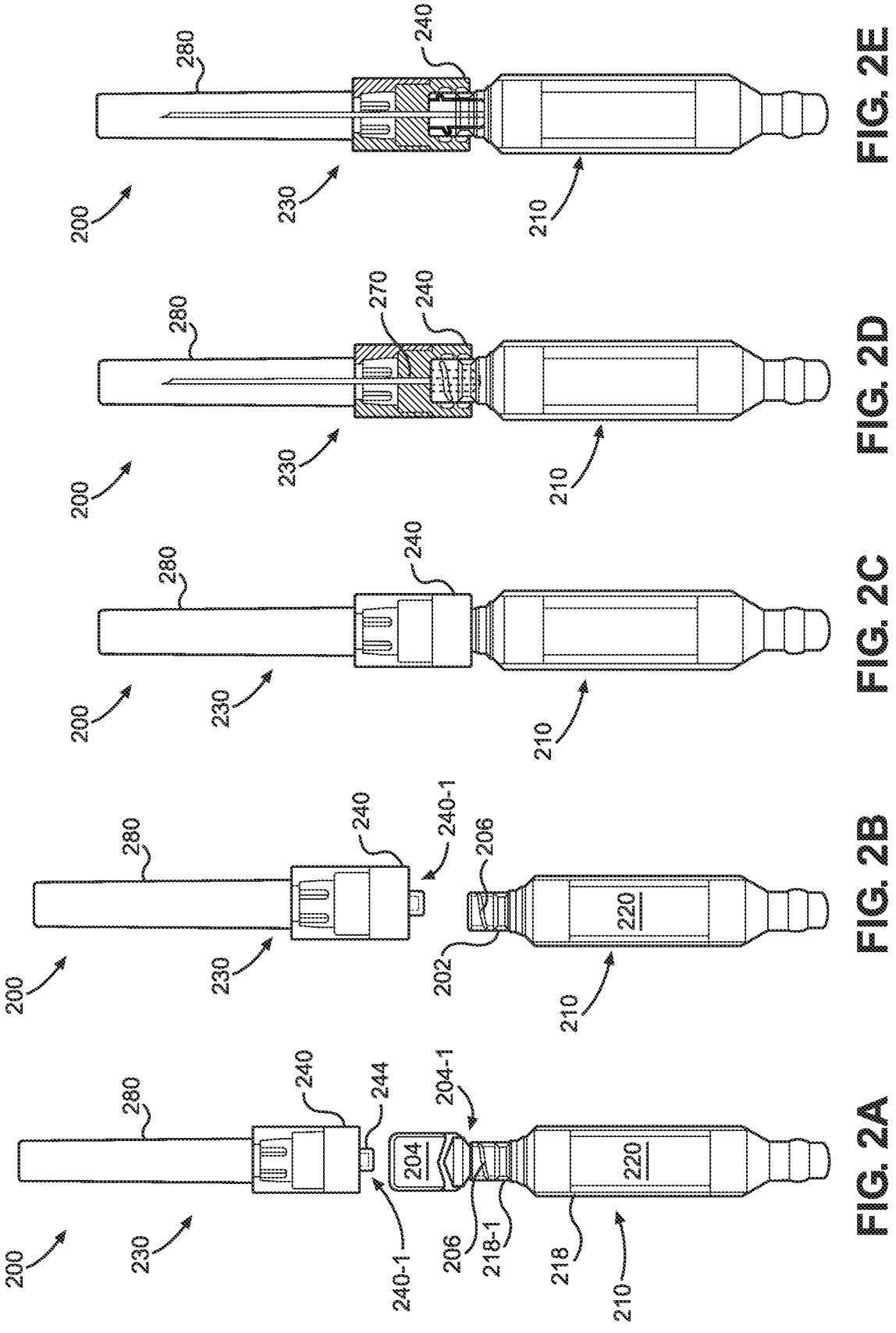
FIG. 2A, FIG. 2B, FIG. 2C, FIG. 2D, FIG. 2E, FIG. 2F, FIG. 2G, and FIG. 2H are various views of a BFS injection system according to some embodiments.

According to some embodiments, the components 210, 230 may be coupled, e.g., in the field and/or in situ, to provide an active pre-filled (e.g., injectable) medical delivery device. As shown in FIG. 2A, for example, the BFS bottle 210 and the administration assembly 230 may be separate. As depicted in FIG. 2B, the removable seal 204 may be removed from the BFS bottle 210 (e.g., at the tear line 204-1) and the administration assembly 230 (and/or the socket 240-1 of the needle hub 240 thereof) may be aligned with the neck 202 (and/or interior passage thereof; not separately labeled) of the BFS bottle 210. According to some embodiments, the administration assembly 230 (and/or the needle hub 240 thereof) may be axially engaged to couple with the BFS bottle 210 via application of a mating axial and/or rotational force, as shown in FIG. 2C, FIG. 2D, FIG. 2E, FIG. 2F, and FIG. 2G. The administration assembly 230 (and/or the needle hub 240 thereof) may be urged onto the neck 202 of the BFS bottle 210, for example, such that the cooperatively shaped interior passage accepts the friction cone 244 and the cooperatively shaped internal threads 242 accept the angled exterior flange 206, thereby selectively and/or removably coupling the BFS bottle 210 and the administration assembly 230 (and/or the needle hub 240 thereof). In some embodiments, the internal threads 242 (and/or other interior features) and/or the angled exterior flange 206 may be shaped such that uncoupling of the BFS bottle 210 and the administration assembly 230 (and/or the needle hub 240 thereof) is mechanically prohibited. In some embodiments, the angled exterior flange 206 may comprise a plurality of angled exterior flanges 206 and/or the internal threads 242 may comprise one or more cooperative and/or mirrored angled interior grooves or tracks. In such a manner, for example, even though the angled exterior flange 206 comprises only the one or more protrusions that are angled on the neck 202, the angled exterior flange(s) 206 may be operable to rotationally engage with the interior threads 242 to mate the BFS bottle 210 with the administration assembly 230.

Figures 2F, 2G, 2H:
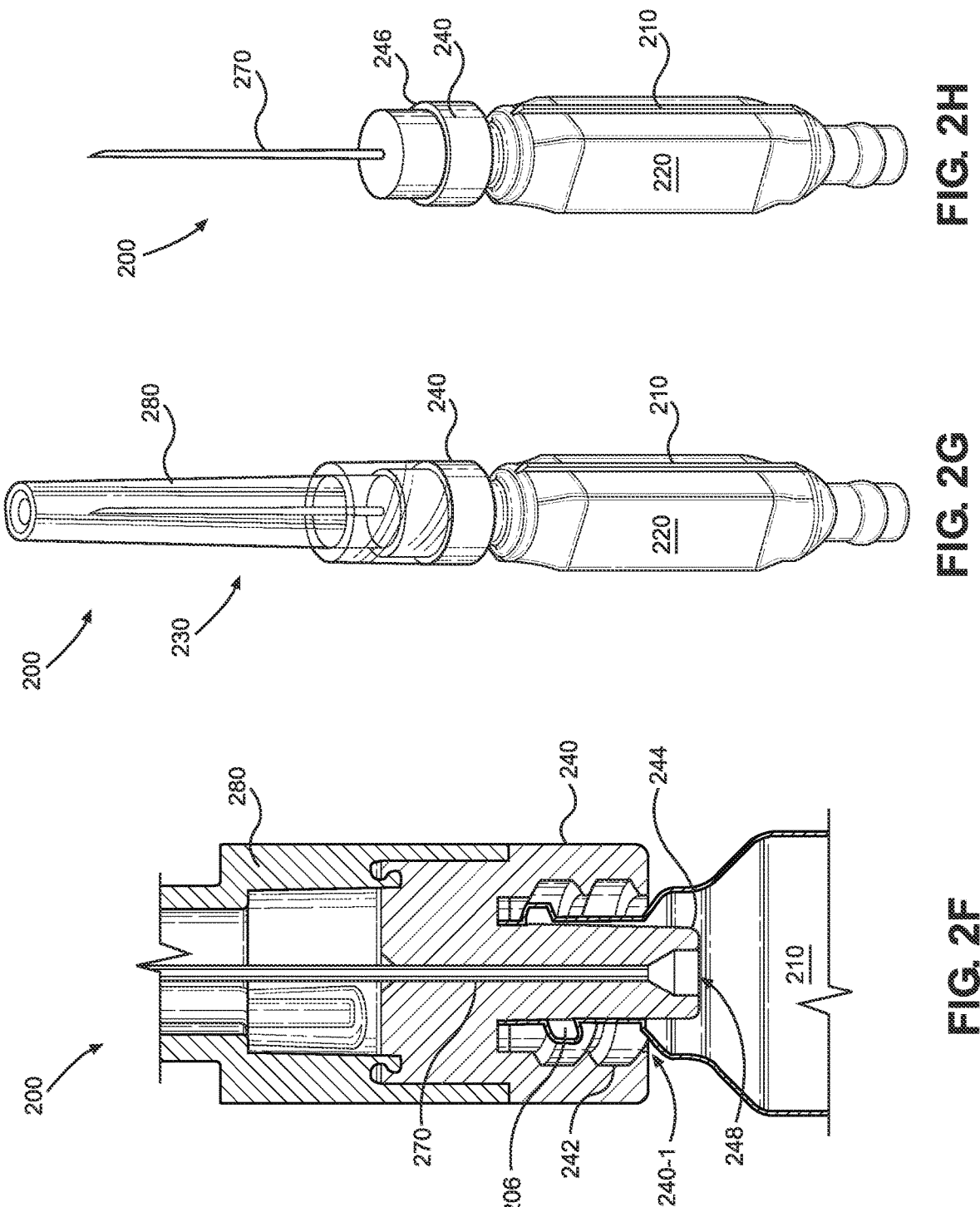

As depicted in FIG. 2F, the neck 202 of the BFS bottle 210 may be urged and/or forced into the socket 240-1 of the needle hub 240 (e.g., rotationally and/or axially) such that a first or proximal end of the administration member 270 is positioned in fluid communication with the reservoir 220 (e.g., via the fluid channel inlet 248 of the friction cone 244). According to some embodiments, the administration member 270 may be inserted into and/or through the needle hub 240, for example, such that it comprises the first, proximal, or receiving end disposed in and/or adjacent to the reservoir 220 and the second, distal, or administration end extending axially distal from the BFS bottle 210. In some embodiments, the administration end and/or a distal portion of the administration member 270 may be housed, shrouded, and/or covered by the cap 280, as shown in FIG. 2G for example. According to some embodiments, the cap 280 may be configured to house the administration member 270 and to removably couple to the needle hub 240 (e.g., by fitting over an external portion thereof and/or by engaging with the external flange 246 thereof). In the case that the cap 280 is removed and the administration assembly 230 is coupled to the BFS bottle 210, the reservoir 220 may accept a compressive (e.g., inward radial) force such as a squeeze force from a user and in response eject the fluid therein through the administration member 270 (e.g., via the fluid channel inlet 248) and, in the case that the distal/administration end of the administration member 270 is engaged with a target/patient, to the target/patient.

According to some embodiments, the needle hub 240 may be utilized to couple and/or mate the administration member 270 with the BFS bottle 210 to provide a mechanism via which the administration member 270 may be effectively coupled to the soft plastic BFS vial 210 in a reliable manner. Due to the nature of the BFS plastic and/or process and/or the small form-factor of the BFS bottle 210, for example, providing standard external threads (not shown; e.g., ¼" NPT threads) directly on the neck 202 would not be a viable option for it would result in an imprecise, unreliable, and/or non-water tight coupling (i.e., the threads would be deformable even if they could be properly manufactured to within the desired tolerances, which itself is not a likely result) between the BFS bottle 210 and, e.g., the needle hub 240. Applicant has realized, for example, that "soft" plastics required for the BFS process are not susceptible to machining due to heat deformation of machined features during formation attempts as well as deformation due to mechanical stress during utilization. As such, standardized screw-on needle hubs (not shown) are not readily compatible for attachment to BFS bottles 210.

In some embodiments, the administration member 270 may include a needle shaped and/or sized for at least one of subcutaneous, intramuscular, intradermal, and intravenous injection of the fluid agent into the patient. For ease of explanation and description, the figures and the description herein generally refer to the administration member 270 as a needle or canula. However, it should be noted that, in other embodiments, the administration member 270 may include a nozzle (not shown) configured to control administration of the fluid agent to the patient. The nozzle may include a spray nozzle, for example, configured to facilitate dispersion of the fluid agent into a spray. Accordingly, a needle hub 240 fitted with a spray nozzle may be particularly useful in the administration of a fluid agent into the nasal passage, for example, or other parts of the body that benefit from a spray application (e.g., ear canal, other orifices). In other embodiments, the nozzle may be configured to facilitate formation of droplets of the fluid agent. Thus, a needle hub 240 including a droplet nozzle may be useful in the administration of a fluid agent by way of droplets, such as administration to the eyes, topical administration, and the like.

As generally understood, the fluid or drug (e.g., stored in the BFS bottle 210 and/or the reservoir 220 thereof) agent may include any type of agent to be injected into a patient (e.g., animal such as a mammal, either human or non-human) and capable of producing an effect (alone, or in combination with an active ingredient). Accordingly, the agent may include, but is not limited to, a vaccine, a drug, a therapeutic agent, a medicament, a diluent, and/or the like. According to some embodiment, either or both of the fluid agent and the active ingredient (i.e., the drug agent and/or components thereof) may be tracked, monitored, checked for compatibility with each other, etc., such as by utilization of electronic data storage devices (not shown) coupled to the various modules or components such as the BFS bottle 210 and/or the administration assembly 230.

According to some embodiments, the needle hub 240 and/or the cap 280 may be composed of a medical grade material. In some embodiments, the needle hub 240 and/or the cap 280 may be composed of a thermoplastic polymer or other "hard" plastic (e.g., greater than 80 on the Rockwell "R" scale), including, but not limited to, polybenzimidazole, acrylonitrile butadiene styrene (ABS), polystyrene, polyvinyl chloride, or the like. In some embodiments, the BFS injection system 200 may be advantageously manufactured (in mass quantities) in separate parts or portions, namely, at least the "soft" plastic BFS bottle 210 portion (e.g., a "first" piece) and the "hard" plastic administration assembly 230 (e.g., the "second" piece), with such different plastic parts/portions being selectively coupled to administer a medication to a patient.

In some embodiments, fewer or more components 202, 204, 204-1, 206, 210, 218, 218-1, 220, 230, 240, 240-1, 242, 244, 246, 248, 270, 280 and/or various configurations of the depicted components 202, 204, 204-1, 206, 210, 218, 218-1, 220, 230, 240, 240-1, 242, 244, 246, 248, 270, 280 may be included in the BFS injection system 200 without deviating from the scope of embodiments described herein. In some embodiments, the components 202, 204, 204-1, 206, 210, 218, 218-1, 220, 230, 240, 240-1, 242, 244, 246, 248, 270, 280 may be similar in configuration and/or functionality to similarly named and/or numbered components as described herein and/or may be utilized to conduct and/or facilitate methods, processes, and/or procedures described herein.

IV. BFS Connection Systems

Figure 3A:
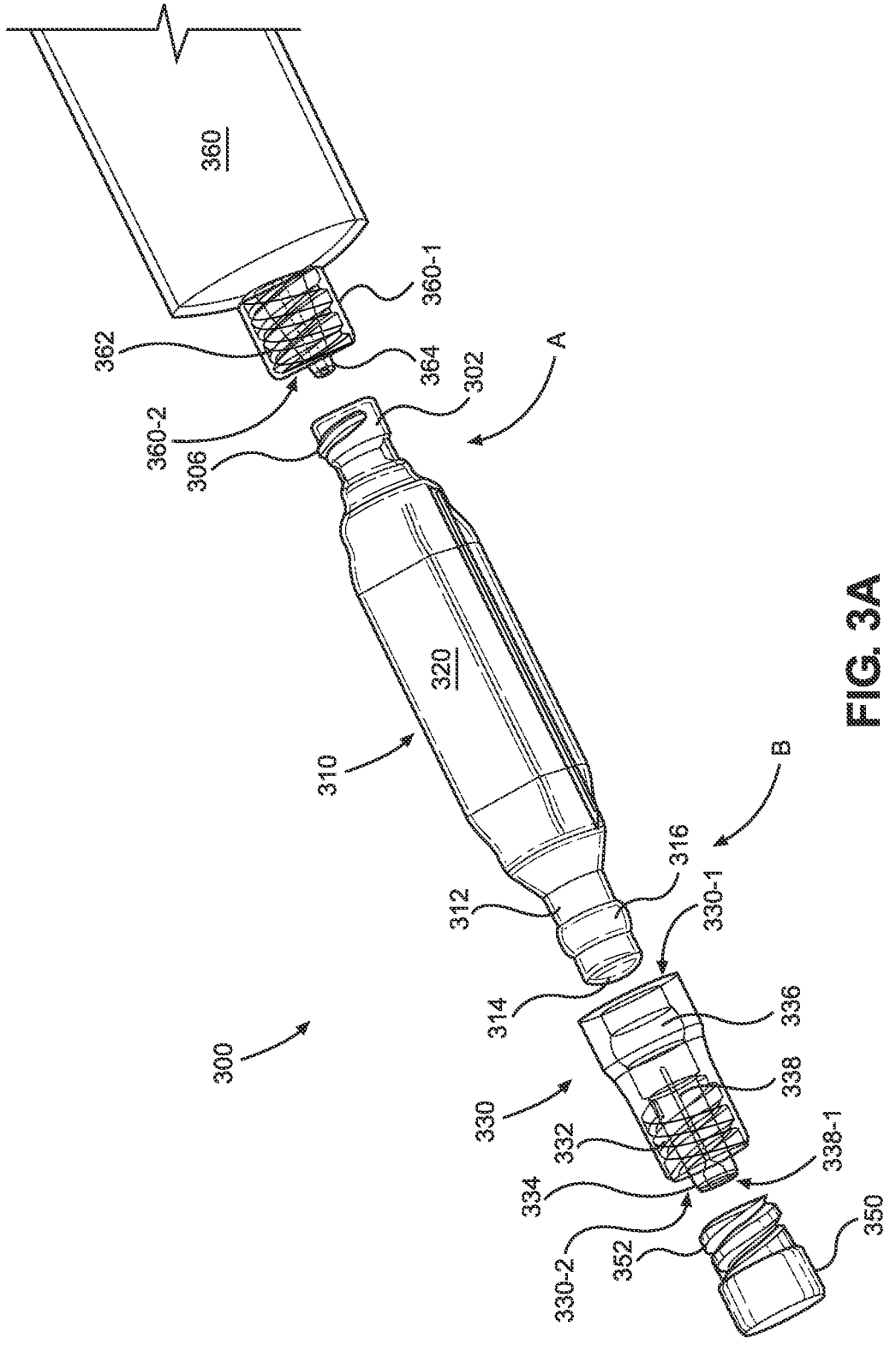
FIG. 3A, FIG. 3B, and FIG. 3C are various views of a BFS connection system according to some embodiments.
Figures 3B, 3C:
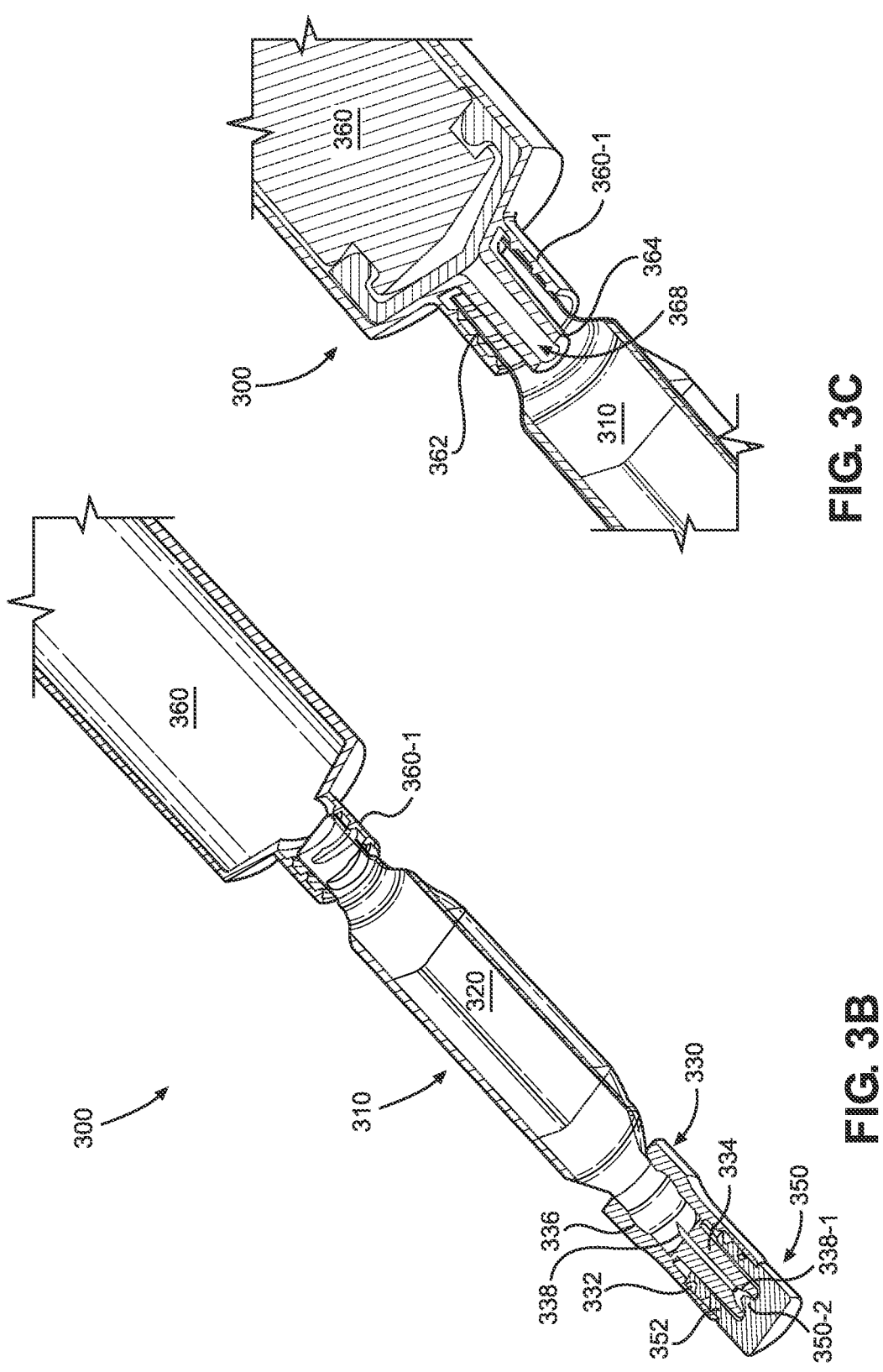

Referring now to FIG. 3A, FIG. 3B, and FIG. 3C, various views of a BFS connection system 300 according to some embodiments are shown. The BFS connection system 300 may comprise similar features and/or configurations and/or may be similar to the BFS injection system 200 of FIG. 2A, FIG. 2B, FIG. 2C, FIG. 2D, FIG. 2E, FIG. 2F, FIG. 2G, and FIG. 2H herein. The BFS connection system 300 may comprise and/or define, for example, a BFS bottle 310 comprising a first end "A" defining a first neck 302 and a first mounting flange 306 and a second end "B" defining a second neck 312, a seal 314, and/or a second mounting flange 316. In some embodiments, the two ends "A" and "B" of the BFS bottle 310 may be configured (as depicted) to advantageously connect to different types of fittings. The first end "A" with the first mounting flange 306, in the case that the first mounting flange 306 is configured as an angled exterior flange as shown, may be configured to rotatably couple to threaded objects (e.g., Luer-style devices) for example, while the second end "B" with the second mounting flange 316 may be configured to axially mate with (e.g., snap into) push-style fittings. In some embodiments, a reservoir (e.g., compressible) 320 may be disposed between the two ends "A" and "B" an may be in fluid communication with the necks 302, 312.

According to some embodiments, a specialized adaptor, assembly, or connector 330 may define a first interior socket or BFS port 330-1 (e.g., at a first connector or assembly end thereof) comprising a seat 336 configured (e.g., sized and shaped) to mate with (e.g. accept) the second mounting flange 316 of the second neck 312 of the BFS bottle 310. In some embodiments, a piercing element 338 (e.g., a canula or tube with at least one pointed end) may be disposed and/or coupled within the BFS port 330-1 such that insertion and/or mating of the second end "B" of the BFS bottle 310 with the connector 330 causes the piercing element 338 to pierce the seal 314. According to some embodiments, the connector 330 may define a second interior socket or outlet port 330-2 (e.g., at a second connector or assembly end thereof) comprising threads 332 and/or an axial projection 334. The axial projection 334 may comprise a cone, for example, that extends from an interior extent (e.g., at a first projection end) of the outlet port 330-2 and/or that defines a fluid outlet 338-1 at an end or extent thereof (e.g., at a second projection end). The axial projection 334 may comprise and/or house the piercing element 338, for example, such that the piercing element 338 is in fluid communication with the fluid outlet 338-1 (and either the BFS port 330-1 or the fluid in the BFS bottle 310, depending upon whether the piercing element 338 has pierced the BFS bottle 310). In some embodiments, a plug 350 may comprise plug threads 352 that are configured to mate with corresponding threads 332 of the connector 330 and/or a projection or nub 350-2 that is configured to seat within the fluid outlet 338-1 in the case that the plug 350 is coupled to the connector 330 (e.g., at the second connector end thereof). While the plug 350 may be utilized to prevent fluid from the reservoir 320 from passing beyond and/or through the connector 330, other fittings (not shown) may also or alternatively be coupled to the connector 330 (e.g., any Luer-style connection fitting).

In some embodiments, the first end "A" of the BFS bottle 310 may be coupled directly to a Luer-style fitting such as a standard syringe 360 comprising a connection neck or collar 360-1 defining a connection port 360-2 and comprising internal or collar threads 362 and/or a projecting cone 364 therein. The first neck 302 may be axially inserted and rotated to engage the first mounting flange 306 with the collar threads 362 of the syringe 360, for example, effectuation a coupling thereof. While not depicted, as the syringe 360 may not comprise a piercing element in some embodiments, a seal (not shown) at the first end "A" and/or at a terminus of the first neck 302 may have already been removed prior to engagement of the first mounting flange 306 with the collar threads 364. In some embodiments, while not depicted, the syringe 360 may be engaged with the first end "A" while the second end "B" ay be coupled to an administration member (not shown; such as a needle hub and/or needle) such that the syringe 360 may be operated to provide pressure (e.g., air pressure), e.g., through a fluid bore 368 and into the BFS bottle 310, to drive the contents of the reservoir 320 through the second end "B" and into/through the administration member. In such a manner, for example, even if the reservoir 320 is collapsible and/or compressible, the syringe 350 may facilitate expelling of the contents thereof by providing an axial pressure force acting through the first end "A".

In some embodiments, fewer or more components 302, 306, 310, 312, 314, 316, 320, 330, 330-1, 330-2, 332, 334, 336, 338, 338-1, 350, 350-2, 352, 360, 360-1, 360-2, 362, 364, 368 and/or various configurations of the depicted components 302, 306, 310, 312, 314, 316, 320, 330, 330-1, 330-2, 332, 334, 336, 338, 338-1, 350, 350-2, 352, 360, 360-1, 360-2, 362, 364, 368 may be included in the BFS connection system 300 without deviating from the scope of embodiments described herein. In some embodiments, the components 302, 306, 310, 312, 314, 316, 320, 330, 330-1, 330-2, 332, 334, 336, 338, 338-1, 350, 350-2, 352, 360, 360-1, 360-2, 362, 364, 368 may be similar in configuration and/or functionality to similarly named and/or numbered components as described herein and/or may be utilized to conduct and/or facilitate methods, processes, and/or procedures described herein.

Figure 4B:
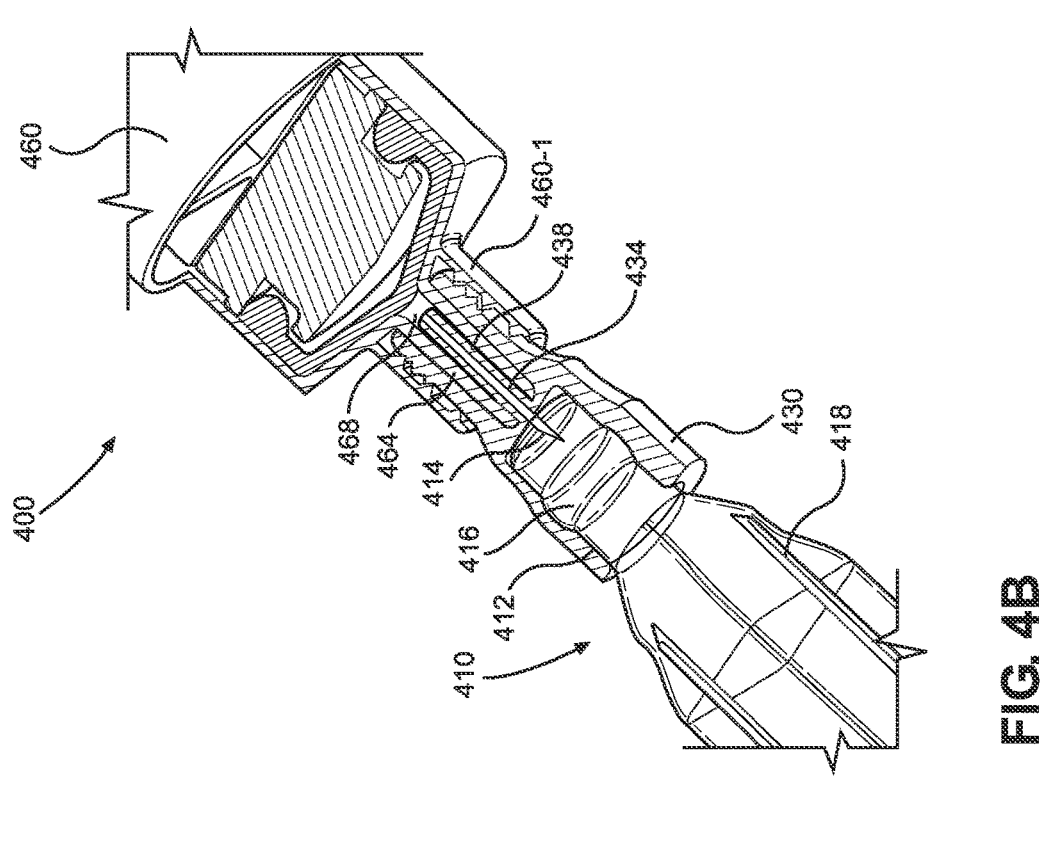
FIG. 4A and FIG. 4B are front cross-section and perspective cross-section views of a BFS connection system according to some embodiments.
Figure 4A:
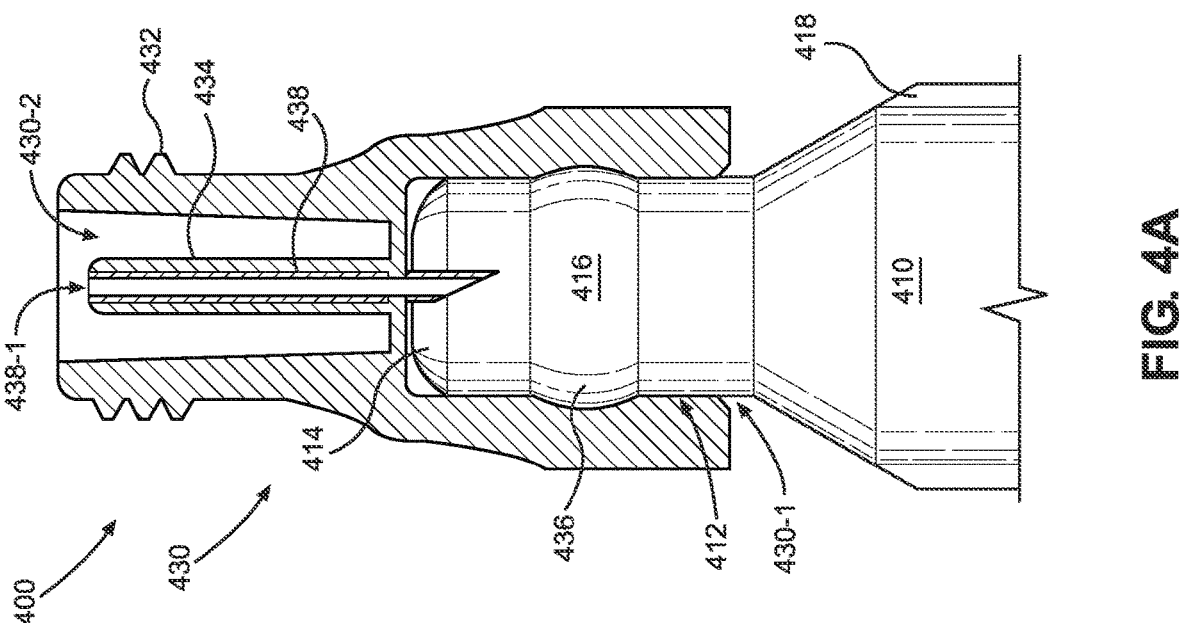

Turning to FIG. 4A and FIG. 4B, front cross-section and perspective cross-section views of a BFS connection system 400 according to some embodiments are shown. The BFS connection system 400 may comprise similar features and/or configurations and/or may be similar to the BFS systems 200, 300 of FIG. 2A, FIG. 2B, FIG. 2C, FIG. 2D, FIG. 2E, FIG. 2F, FIG. 2G, FIG. 2H, FIG. 3A, FIG. 3B, and/or FIG. 3C herein. The BFS connection system 400 may comprise and/or define, for example, a BFS bottle 410 comprising a neck 412, a seal 414, and/or an exterior rounded (e.g., "doughnut"-shaped) flange 416. According to some embodiments, the BFS bottle 410 may comprise a side flange 418 that extends axially along one or more edges of the BFS bottle 410. In some embodiments, the BFS connection system 400 may comprise a specialized adapter or connector 430 that is configured to selectively and reliably mate with the BFS bottle 410 via a first connector end and to connect to/mate with threaded fittings at a second connector end. According to some embodiments, the connector 430 may define a first interior socket or BFS port 430-1 (e.g., at the first connector end thereof) and/or a second interior socket or outlet port 430-2 (e.g., at the second connector end thereof). In some embodiments, the connector 430 and/or the outlet port 430-2 may comprise and/or define threads 432 and/or an axial projection 434 (extending axially outward from the outlet port 430-2). In some embodiments, the connector 430 and/or the BFS port 430-1 may comprise and/or define a mounting feature or seat 436 that is configured to mate with (e.g., receive and/or retain) a corresponding one or more of the exterior rounded flange 416 and the side flange 418 of the BFS bottle 410. In the case that the seat 436 is configured (e.g., sized and shaped) to accept the exterior rounded flange 416, the seat 436 may comprise an interior radial channel 436, as shown.

In some embodiments, a piercing element 438 may be disposed and/or coupled within the BFS port 430-1 such that insertion and/or mating of the neck 412 of the BFS bottle 410 with the connector 430 causes the piercing element 438 to pierce the seal 414. According to some embodiments, the piercing element 438 may be disposed through and/or retained by the axial projection 434. In some embodiments, the piercing element 438 may comprise a pointed (and/or sharpened) metal tube. In such a manner, for example, the piercing element 438 may comprise a piercing end disposed within the BFS port 430-1 and an outlet end disposed to provide, form, and/or define a fluid outlet 438-1 at the tip of the axial projection 434.

According to some embodiments, the threads 432 may comprise external threads 432 such that, for example, a standard Luer-style syringe 460 may be rotatably coupled thereto (as shown in FIG. 4B). The syringe 460 may comprise a connection collar 460-1 into which the threads 432 are engaged, for example, and/or may comprise a friction cone 464 that fits into the outlet port 430-2 of the connector 430. According to some embodiments, the axial projection 434 may be shaped and/or sized to fit or nest within a fluid bore 468 of the syringe 460 (e.g., formed within the friction cone 464 thereof). In such a manner, for example, the standard syringe 460 with a Luer-style threaded coupling may be selectively mated with the connector 430 that pierces the seal 414 of the BFS bottle 410, thereby placing the contents of the BFS bottle 410 in fluid communication with the syringe 460. The mating and/or coupling of the connector 430 and the syringe 460 (and/or other similarly configured medical fluid device; not shown) may, for example, define a fluid pathway from the pointed/piercing end of the piercing element 438, through the axial projection 434 (and accordingly through the friction cone 464 in which the axial projection 434 is nested), and out through the fluid outlet 438-1 and into the fluid bore 468. The syringe 460 may then be utilized, for example, to draw fluid from the BFS bottle 410, insert fluid into the BFS bottle 410, and/or apply fluid pressure into the BFS bottle 410.

In some embodiments, fewer or more components 410, 412, 414, 416, 418, 430, 430-1, 430-2, 432, 434, 436, 438, 438-1, 460, 460-1, 464, 468 and/or various configurations of the depicted components 410, 412, 414, 416, 418, 430, 430-1, 430-2, 432, 434, 436, 438, 438-1, 460, 460-1, 464, 468 may be included in the BFS connection system 400 without deviating from the scope of embodiments described herein. In some embodiments, the components 410, 412, 414, 416, 418, 430, 430-1, 430-2, 432, 434, 436, 438, 438-1, 460, 460-1, 464, 468 may be similar in configuration and/or functionality to similarly named and/or numbered components as described herein and/or may be utilized to conduct and/or facilitate methods, processes, and/or procedures described herein.

Figures 5A, 5B:
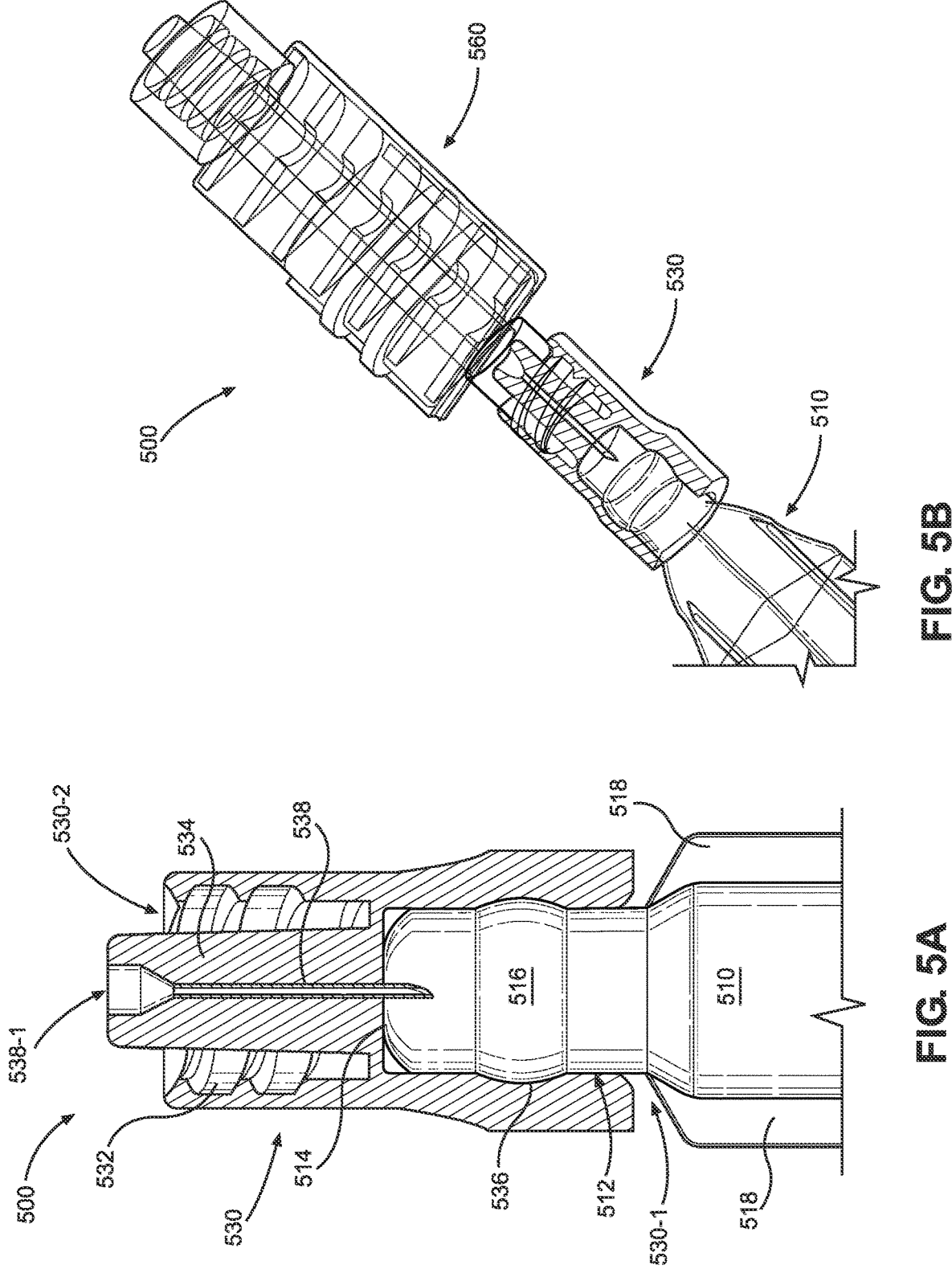
FIG. 5A, FIG. 5B, FIG. 5C, FIG. 5D, FIG. 5E, FIG. 5F, FIG. 5G, FIG. 5H, FIG. 5I, and FIG. 5J are various views of a BFS connection system according to some embodiments.

Referring finally to FIG. 5A, FIG. 5B, FIG. 5C, FIG. 5D, FIG. 5E, FIG. 5F, FIG. 5G, FIG. 5H, FIG. 5I, and FIG. 5J, various views of a BFS connection system 500 according to some embodiments are shown. The BFS connection system 500 may comprise similar features and/or configurations and/or may be similar to the BFS systems 200, 300, 400 of FIG. 2A, FIG. 2B, FIG. 2C, FIG. 2D, FIG. 2E, FIG. 2F, FIG. 2G, FIG. 2H, FIG. 3A, FIG. 3B, FIG. 3C, FIG. 4A, and/or FIG. 4B herein. The BFS connection system 500 may comprise and/or define, for example, a BFS bottle 510 comprising a neck 512, a seal 514, and/or an exterior rounded (e.g., "doughnut"-shaped) flange 516. According to some embodiments, the BFS bottle 510 may comprise a side flange 518 that extends axially along one or more edges of the BFS bottle 510 (e.g., two (2) symmetric side flanges 518 extending radially outward from and axially along two (2) opposite sides of the BFS bottles 510, as depicted in FIG. 5A).

In some embodiments, the BFS connection system 500 may comprise a specialized adapter or connector 530 that is configured to selectively and reliably mate with the BFS bottle 510 via a first end and to connect to/mate with threaded fittings at a second end. According to some embodiments, the connector 530 may define an interior socket or BFS port 530-1 (e.g., at the first connector end thereof) and/or a second interior socket or outlet port 530-2 (e.g., at the second connector end thereof). In some embodiments, the connector 530 and/or the outlet port 530-2 may comprise and/or define threads 532 and/or an axial projection 534 (extending axially outward from the outlet port 530-2). In some embodiments, the connector 530 and/or the BFS port 530-1 may comprise and/or define a mounting feature or seat 536 that is configured to mate with (e.g., receive and/or retain) a corresponding one or more of the exterior rounded flange 516 and the side flange 518 of the BFS bottle 510. In the case that the seat 536 is configured (e.g., sized and shaped) to accept the exterior rounded flange 516, the seat 536 may comprise an interior radial channel 536, as shown.

In some embodiments, a piercing element 538 may be disposed and/or coupled within the BFS port 530-1 such that insertion and/or mating of the neck 512 of the BFS bottle 510 with the connector 530 causes the piercing element 538 to pierce the seal 514. According to some embodiments, the piercing element 538 may be disposed through and/or retained by the axial projection 534. In some embodiments, the piercing element 538 may comprise a pointed (and/or sharpened) metal tube. In such a manner, for example, the piercing element 538 may comprise a piercing end disposed within the BFS port 530-1 and an outlet end disposed to provide, form, and/or define a fluid outlet 538-1 at the tip of the axial projection 534.

Figures 5C, 5D, 5E, 5F, 5G:
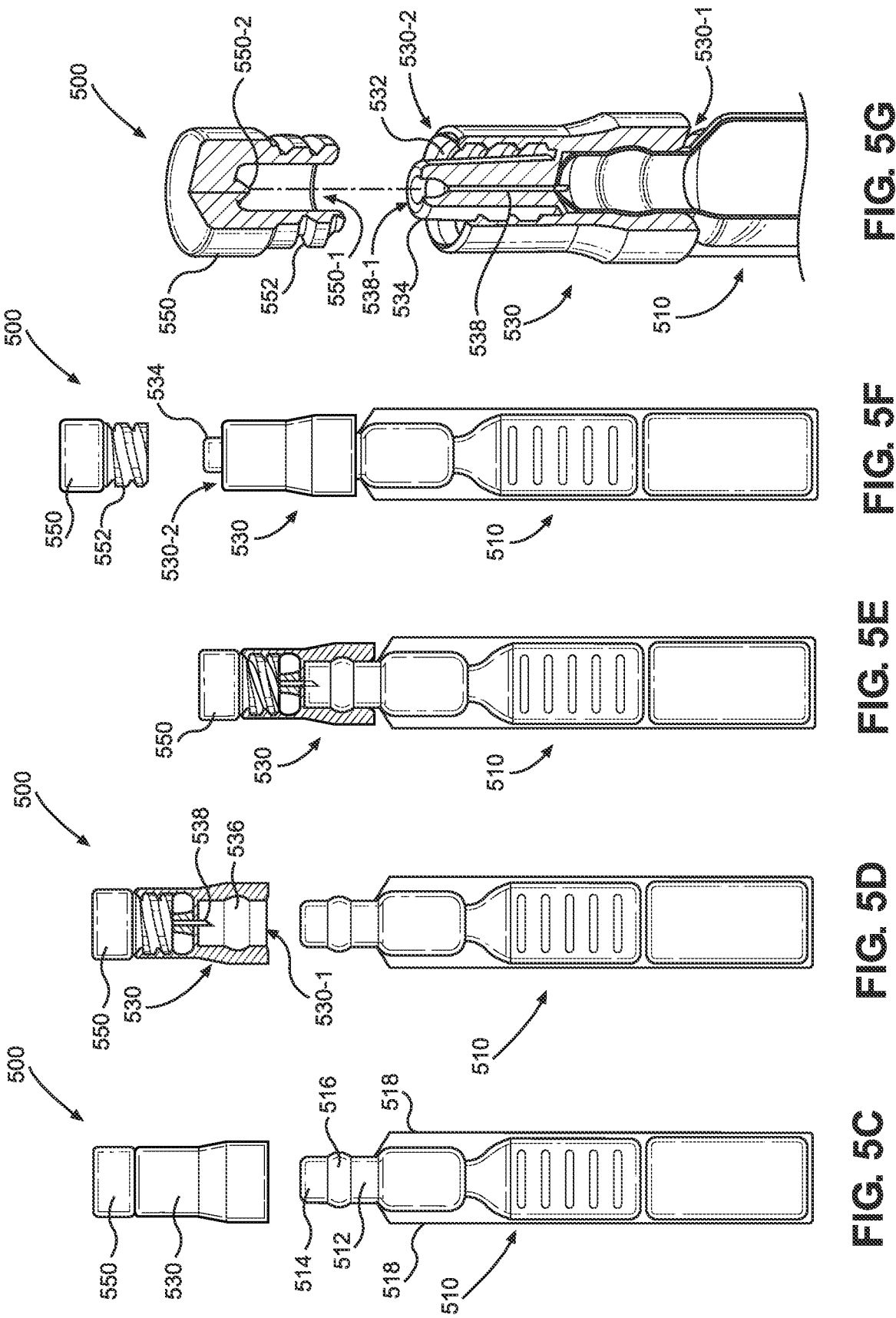

According to some embodiments, the threads 532 may comprise internal threads 532 such that, for example, a Luer-style plug 550 and/or other threaded medical device 560 may be rotatably coupled thereto (as shown in FIG. 5B, FIG. 5C, FIG. 5D, FIG. 5E, FIG. 5F, FIG. 5G, FIG. 5H, FIG. 5I, and FIG. 5J). In such a manner, for example, the device 560 with a Luer-style threaded coupling may be selectively mated with the connector 530 that pierces the seal 514 of the BFS bottle 510, thereby placing the contents of the BFS bottle 510 in fluid communication with the device 560. The device 560 may then be utilized, for example, to draw fluid from the BFS bottle 510, insert fluid into the BFS bottle 510, and/or apply fluid pressure into the BFS bottle 510. According to some embodiments, the plug 550 may comprise exterior threads 552 configured to mate with the internal threads 532 of the connector 530. As depicted in FIG. 5C and FIG. 5D, the connector 530 and the plug 550 may be coupled and then advanced axially such that the neck 512 of the BFS bottle 510 snaps into the BFS port 530-1 of the connector 530, as depicted in FIG. 5E. As shown in FIG. 5A, FIG. 5G, FIG. 5H, and FIG. 5I, in the case that the exterior rounded flange 516 of the neck 512 of the BFS bottle 510 becomes seated in the seat 536 of the BFS port 530-1 of the connector 530, the piercing element 538 may breach the seal 514 thereby establishing a fluid communication between the contents of the BFS bottle 510 and a distal end of the connector 530. In the case that the plug 550 is installed (FIG. 5E), the fluid of the BFS bottle 510 may be retained within the BFS bottle 510 and the connector 530. In some embodiments, after the connector 530 is installed on the BFS bottle 510, the plug 550 may be selectively removed (FIG. 5F, FIG. 5G, FIG. 5H, and FIG. 5I) such that the fluid from the BFS bottle 510 may be dispensed (e.g., through the distal end of the connector 530). As depicted in FIG. 5B, one or more threaded fittings or objects such as needle hubs (not shown) and/or the device 560 may be coupled to the distal end of the connector 530 to extract, add, pressurize, dispense, and/or administer the fluid of the BFS bottle 510.

Figures 5H, 5I, 5J:
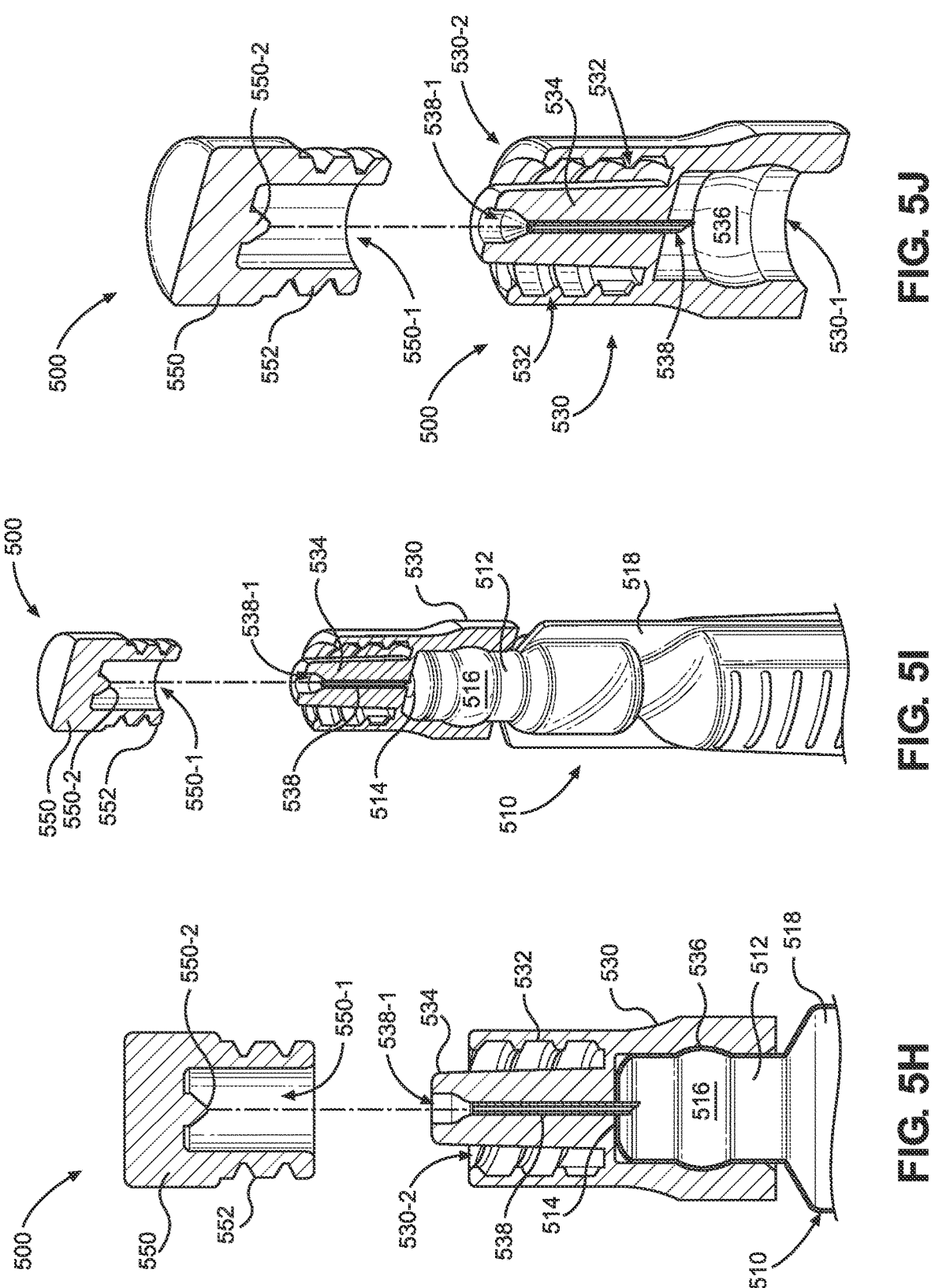

In some embodiments, the plug 550 may define a plug volume 550-1 and/or an interior projection or nub 550-2. According to some embodiments, in the case that the exterior threads 552 of the plug 550 are engaged with the internal threads 532 of the connector 530, the axial projection 534 may extend into and/or fit or seat within the plug volume 550-1. In some embodiments, the nub 550-2 may align with and/or be sized and/or shaped to seat in the fluid outlet 538-1 at the tip of the axial projection 534. In such a manner, for example, any fluid within the BFS bottle 510 and/or the piercing element 538 may be retained and/or prevented from escaping the connector 530 as the plug 550 may seal the outlet port 530-2. According to some embodiments, such as depicted in FIG. 5J, the connector 530 and/or the plug 550 may exist and/or be utilized separately from the BFS bottle 510. In some embodiments, and with reference to FIG. 5H, the connector 530 and/or the seat 536 (or other mounting feature thereof) may engage with (not shown) the side flanges 518. The side flanges 518 may extend axially further toward or along the neck 502, for example, and/or the connector 530 may extend axially further toward the side flanges 518, e.g., such that the connector 530 is retained on the BFS bottle 510 via the side flanges 518.

In some embodiments, fewer or more components 510, 512, 514, 516, 518, 530, 530-1, 530-2, 532, 534, 536, 538, 538-1, 550, 550-1, 550-2, 552, 560 and/or various configurations of the depicted components 510, 512, 514, 516, 518, 530, 530-1, 530-2, 532, 534, 536, 538, 538-1, 550, 550-1, 550-2, 552, 560 may be included in the BFS connection system 500 without deviating from the scope of embodiments described herein. In some embodiments, the components 510, 512, 514, 516, 518, 530, 530-1, 530-2, 532, 534, 536, 538, 538-1, 550, 550-1, 550-2, 552, 560 may be similar in configuration and/or functionality to similarly named and/or numbered components as described herein and/or may be utilized to conduct and/or facilitate methods, processes, and/or procedures described herein.

Figure 6B:
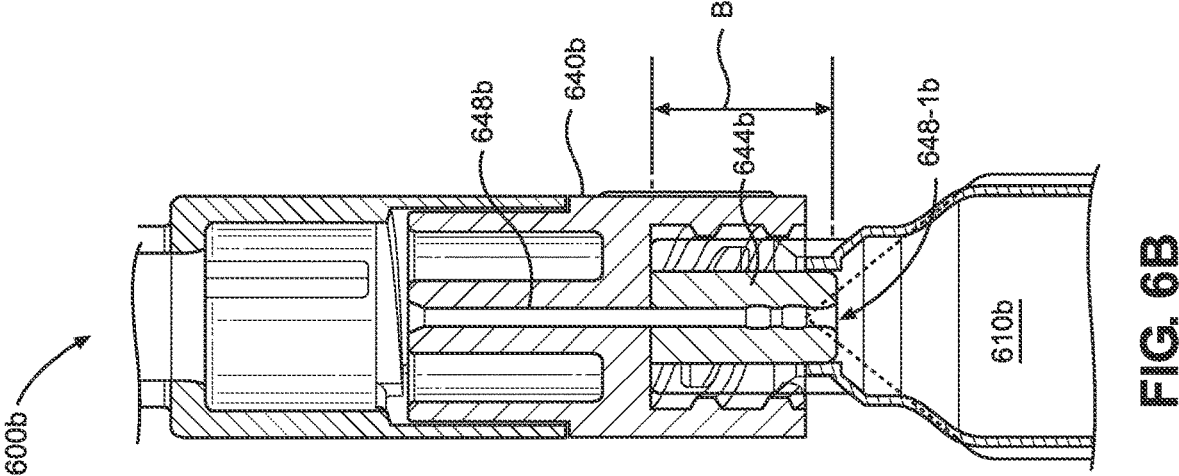
FIGS. 6A and 6B are front cross-section views of two versions of a BFS connection system according to some embodiments.
Figure 6A:
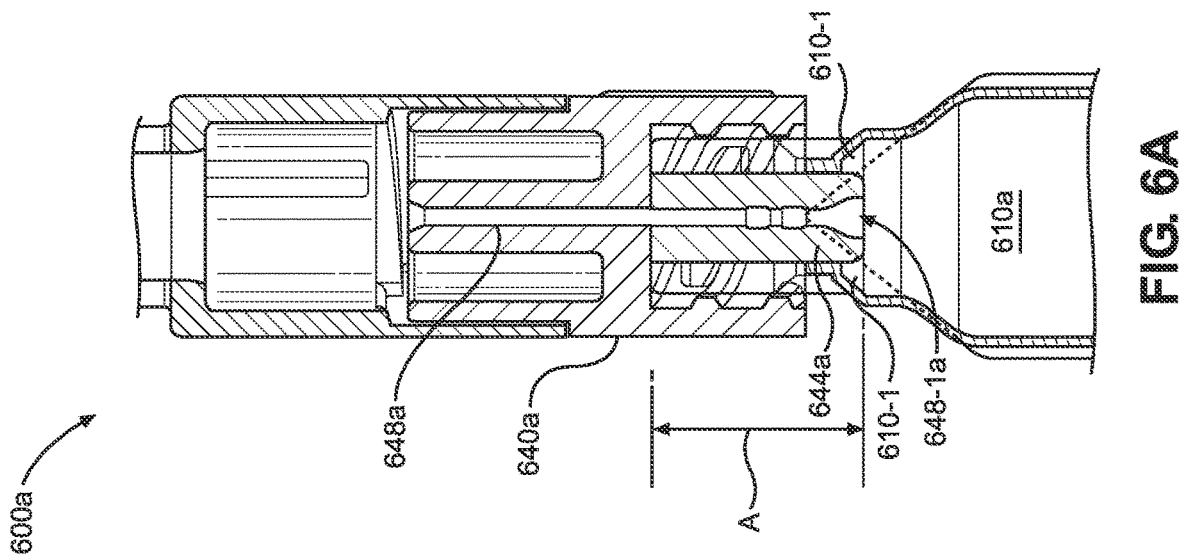

Referring now to FIGS. 6A and 6B, front cross-section views of two versions of a BFS connection system 600a-b are shown. The BFS connection systems 600a-b illustrated in FIG. 6A and/or FIG. 6B may comprise, for example, embodiments of a BFS connection assembly system such as those illustrated as BFS systems 200, 300, 400, 500 of FIG. 2A, FIG. 2B, FIG. 2C, FIG. 2D, FIG. 2E, FIG. 2F, FIG. 2G, FIG. 2H, FIG. 3A, FIG. 3B, FIG. 3C, FIG. 4A, FIG. 4B, FIG. 5A, FIG. 5B, FIG. 5C, FIG. 5D, FIG. 5E, FIG. 5F, FIG. 5G, FIG. 5H, FIG. 5I, and/or FIG. 5J herein. In some embodiments, the BFS connection systems 600a-b may comprise BFS bottles 610a-b that are coupled to (e.g., mated with) respective adapters 640a-b. According to some embodiments, the adaptors 640a-b may comprise and/or define axial projections 644a-b that comprise and/or define fluid channels 648a-b therethrough. In some embodiments, the fluid channels 648a-b may be open at a first or inlet end that is disposed and/or formed, for example, at a tip or extent of the axial projections 644a-b, thereby defining fluid channel inlets 648a-1a, 648-1b. According to some embodiments, the axial projections 644a-b may extend into the BFS bottles 610a-b such that fluid from the BFS vials 610a-b may be expelled into the fluid channel inlets 648a-1a, 648-1b and through the fluid channels 648a-b. According to some embodiments, each of the axial projections 644a-b may comprise and/or define a length "A" or "B", respectively.

In some embodiments, a first axial projection 644a may comprise a first length "A" that may, for example, be similar to and/or in accordance with the ISO 80369-7:2021 "Small-bore connectors for liquids and gases in healthcare applications—Part 7: Connectors for intravascular or hypodermic applications" standard published by the International Organization for Standardization of Geneva, Switzerland (May, 2021). The first length "A", in some embodiments, may be seven and on half millimeters (7.5-mm). According to some embodiments, a second axial projection 644b may comprise a second length "B" that is shorter than the first length "A". The length of the second axial projection 644b may be modified (e.g., shortened), for example, in order to achieve certain desired benefits.

Applicant has recognized, for example, that the first axial projection 644a may be configured or manufactured in different lengths (e.g., the first length "A") and that the different lengths may impact one or more performance characteristics (e.g., hold up volume or dose delivery volume) of a first version of the BFS connection system 600a. As shown by the dotted lines within a first BFS bottle 610a of FIG. 6A, for example, fluid flow toward a first fluid channel inlet 648-1a may deviate from the interior side walls of the first BFS bottle 610a. Such a deviation or misalignment may, for example, create and/or define a ponding area 690 that is subject to reduced fluid flow velocity, eddy currents, etc. In the case that the first BFS connection system 600a is inverted so that the fluid flows downward (e.g., at least in part being aligned with gravitational force), some of the fluid (e.g., particularly in the case of a liquid) may be held up in the ponding area(s) 690 and accordingly, the full dose filled into the first BFS bottle 610a may not be delivered. Particularly in cases where the filled dose is small (e.g., one to ten milliliters (1-10-ml), and amount of dosage retained, delayed, or held up in the ponding area(s) 690 can comprises a significant percentage of the filled dose that is not readily delivered by the first BFS connection system 600a.

In some embodiments, the second axial projection 644b may be provided with the shorter second length "B" that reduces or eliminates the projection of the tip of the second axial projection 644b into a second BFS bottle 610b. Applicant has realized, for example, that configuring the second length "B" to be between one and three millimeters (1-3- mm) shorter than the first length "A" can significantly decrease or even eliminate hold up volume issues due to the existence of the ponding area(s) 690. The shortened second axial projection 644b may, for example, place a second fluid channel inlet 648-1b in more direct alignment with the fluid flow inside of the second BFS bottle 610b (e.g., as compared to the first axial projection 644a and the first BFS bottles 610a), which may result in a larger percentage of the volume of filled fluid/medicament in the second BFS bottles 610b being expelled through a second fluid channel 648b. While a particular style of adapter 640a-b is shown in FIG. 6A and FIG. 6B to illustrate the comparison between the first and second lengths "A" and "B" of the first and second axial projections 644a-b, any type of device that utilizes an axial projection 644a-b such as a cylinder or tapered cone (e.g., a Luer taper) may be similarly adjusted (e.g., shortened) to reduce or prevent dose delivery issues.

In some embodiments, fewer or more components 610a-b, 640a-b, 644a-b, 648a-b, 648-1a, 648-1b, 690 and/or various configurations of the depicted components 610a-b, 640a-b, 644a-b, 648a-b, 648-1a, 648-1b, 690 may be included in the BFS connection system 600a-b without deviating from the scope of embodiments described herein. In some embodiments, the components 610a-b, 640a-b, 644a-b, 648a-b, 648-1a, 648-1b, 690 may be similar in configuration and/or functionality to similarly named and/or numbered components as described herein and/or may be utilized to conduct and/or facilitate methods, processes, and/or procedures described herein.

Referring now to FIG. 7A, FIG. 7B, FIG. 7C, FIG. 7D, FIG. 7E and FIG. 7F, various views of a BFS connection system 700 according to some embodiments are shown. The BFS connection system 700 may comprise similar features and/or configurations and/or may be similar to the BFS systems 200, 300, 400, 500, 600 of FIG. 2A, FIG. 2B, FIG. 2C, FIG. 2D, FIG. 2E, FIG. 2F, FIG. 2G, FIG. 2H, FIG. 3A, FIG. 3B, FIG. 3C, FIG. 4A, FIG. 4B, FIG. 5A, FIG. 5B, FIG. 5C, FIG. 5D, FIG. 5E, FIG. 5F, FIG. 5G, FIG. 5H, FIG. 5I, FIG. 5J, FIG. 6A, and/or FIG. 6B herein. The BFS connection system 700 may comprise and/or define, for example, a BFS bottle 710 comprising a neck 712, a seal 714, and/or an exterior rounded (e.g., "doughnut"-shaped) flange 716. According to some embodiments, the BFS bottle 710 may comprise a side flange 718 that extends axially along one or more edges of the BFS bottle 710 and/or a collapsible or compressible reservoir 720 that is in fluid communication with the neck 712 (e.g., an sealed by the seal 714). In some embodiments, the BFS connection system 700 may comprise a specialized adapter or connector 730 that is configured to selectively and reliably mate with the BFS bottle 710 via a first connector end and to connect to/mate with threaded fittings at a second connector end. According to some embodiments, the connector 730 may define a first interior socket or BFS port 730-1 (e.g., at the first connector end thereof) and/or a second interior socket or outlet port 730-2 (e.g., at the second connector end thereof). In some embodiments, the connector 730 may comprise and/or define an aperture 730-3 formed and/or cut in a side-wall of the connector 730. According to some embodiments, the connector 730 and/or the outlet port 730-2 may comprise and/or define threads 732 and/or an axial projection 734 (extending axially outward from the outlet port 730-2). In some embodiments, the connector 730 and/or the BFS port 730-1 may comprise and/or define a mounting feature or seat 736 that is configured to mate with (e.g., receive and/or retain) a corresponding one or more of the exterior rounded flange 716 and the side flange 718 of the BFS bottle 710. In the case that the seat 736 is configured (e.g., sized and shaped) to accept the side flange 718, the seat 736 may comprise and/or define a track 736-1 and/or an axial slit 736-2.

In some embodiments, a piercing element 738 may be disposed and/or coupled within the BFS port 730-1 such that insertion and/or mating of the neck 712 of the BFS bottle 710 with the connector 730 causes the piercing element 738 to pierce the seal 714. According to some embodiments, the piercing element 738 may be disposed through and/or retained by the axial projection 734. In some embodiments, the piercing element 738 may comprise a pointed (and/or sharpened) metal tube. In such a manner, for example, the piercing element 738 may comprise a piercing end disposed within the BFS port 730-1 and an outlet end disposed to provide, form, and/or define a fluid outlet 738-1 at the tip of the axial projection 734.

According to some embodiments, the threads 732 may comprise external threads 732 such that, for example, a standard Luer-style syringe 760 may be rotatably coupled thereto (as shown). The syringe 760 may comprise a connection collar 760-1 defining interior threads 762 into or onto which the threads 732 are engaged, for example, and/or may comprise a friction cone 764 that fits into the outlet port 730-2 of the connector 730. According to some embodiments, the syringe 760 may comprise a piston 766 that may be utilized to create a vacuum to extract fluid from and/or generate pressure to insert fluid into, the BFS bottle 710. In some embodiments, the axial projection 734 may be shaped and/or sized to fit or nest within a fluid bore 768 of the syringe 760 (e.g., formed within the friction cone 764 thereof). In such a manner, for example, the standard syringe 760 with a Luer-style threaded coupling (e.g., the connection collar 7601-, interior threads 762, and/or friction cone 764) may be selectively mated with the connector 730 that pierces the seal 714 of the BFS bottle 710, thereby placing the contents of the BFS bottle 710 in fluid communication with the syringe 760. The mating and/or coupling of the connector 730 and the syringe 760 (and/or other similarly configured medical fluid device; not shown) may, for example, define a fluid pathway from the pointed/piercing end of the piercing element 738, through the axial projection 734 (and accordingly through the friction cone 764 in which the axial projection 734 is nested), and out through the fluid outlet 738-1 and into the fluid bore 768. The syringe 760 may then be utilized, for example, to draw fluid from the BFS bottle 710, insert fluid into the BFS bottle 710, and/or apply fluid pressure into the BFS bottle 710.

In some embodiments, the BFS bottle 710 may comprises two (2) side flanges 718 that are engaged with the seat 736 in the case that the connector 730 is coupled to the BFS bottle 710. The connector 730 may be slid into and/or over the neck 712 of the BFS bottle 710, for example, such that the side flanges 718 enter into the tracks 736-1 and/or protrude into and/or through the axial slits 736-2. According to some embodiments, the side flanges 718 may fit into one or more of the tracks 736-1 and the axial slits 736-2 in a friction-fit and/or interference fit manner so that some amount of force (e.g., one to three pounds (1-3-lbs)) may be required to engage or disengage the BFS bottle 710 with/ from the connector 730. In some embodiments, the side flanges 718 may lock into and/or otherwise be retained by the tracks 736-1 and/or the axial slits 736-2, e.g., such that removal of the BFS bottle 710 from the connector 730 is mechanically prohibited or prevented.

Figure 7A:
FIG. 7A, FIG. 7B, FIG. 7C, FIG. 7D, FIG. 7E and FIG. 7F are various views of a BFS connection system according to some embodiments.
Figure 7B:
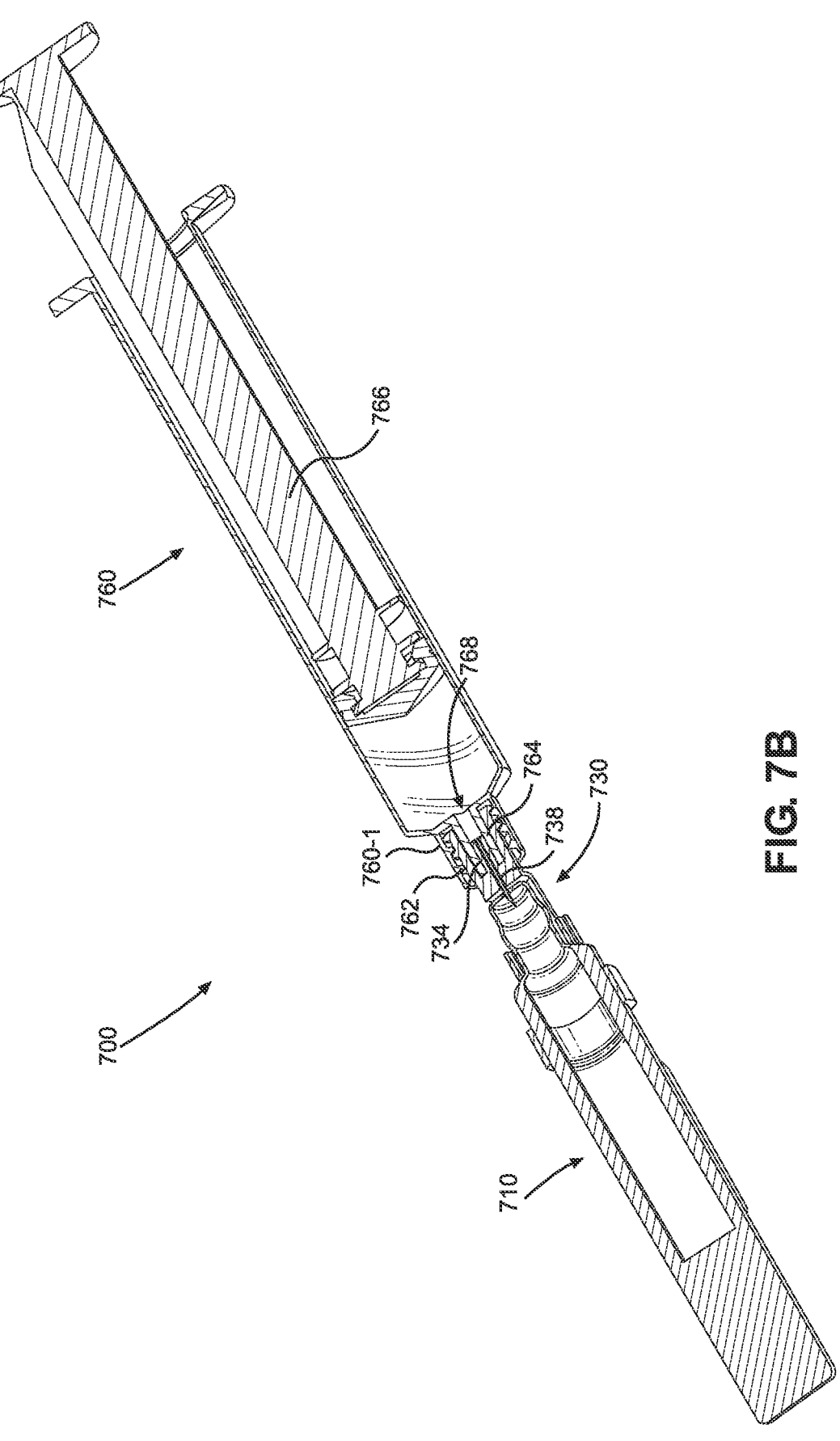
Figure 7C:
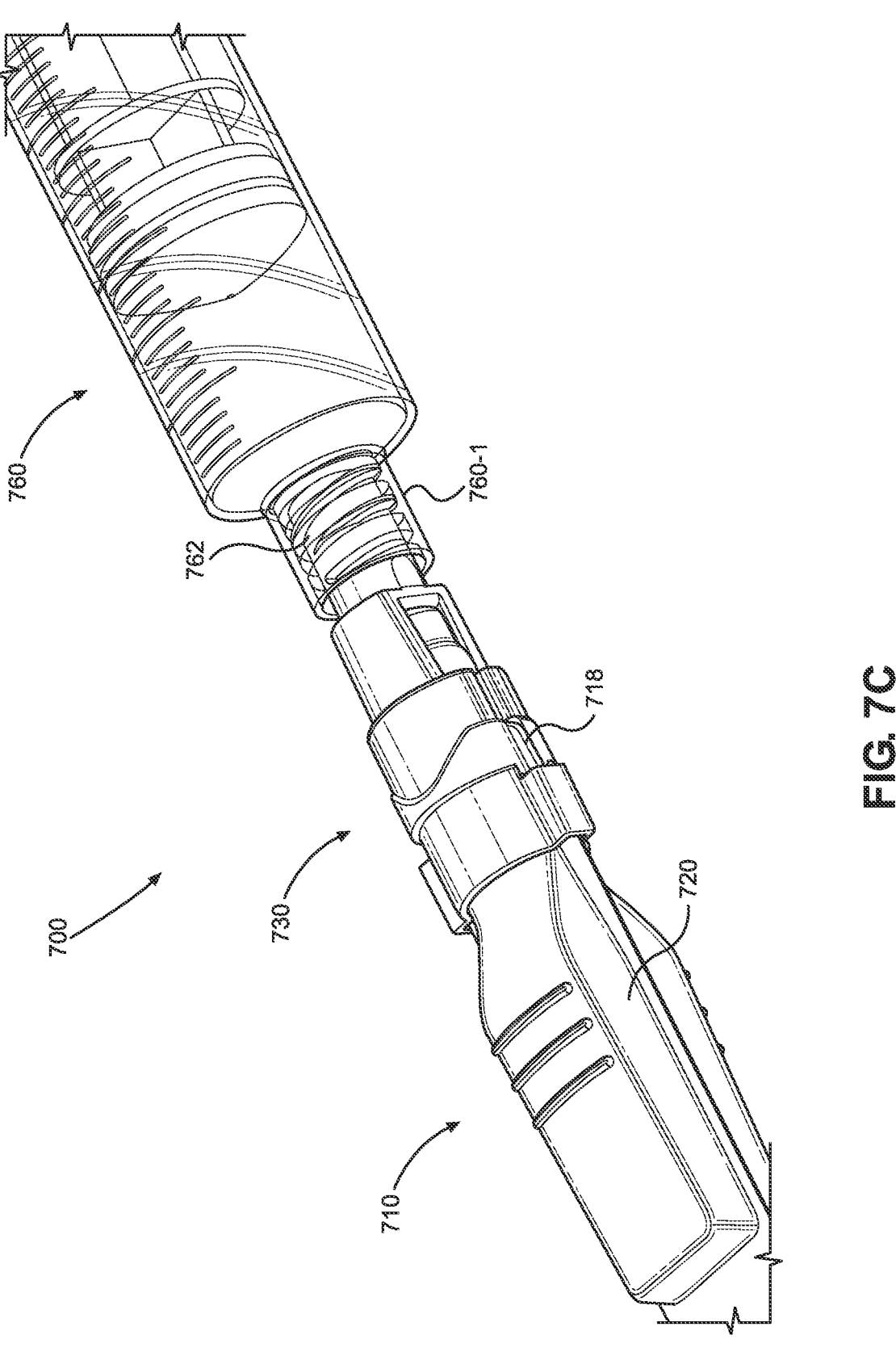
Figure 7D:
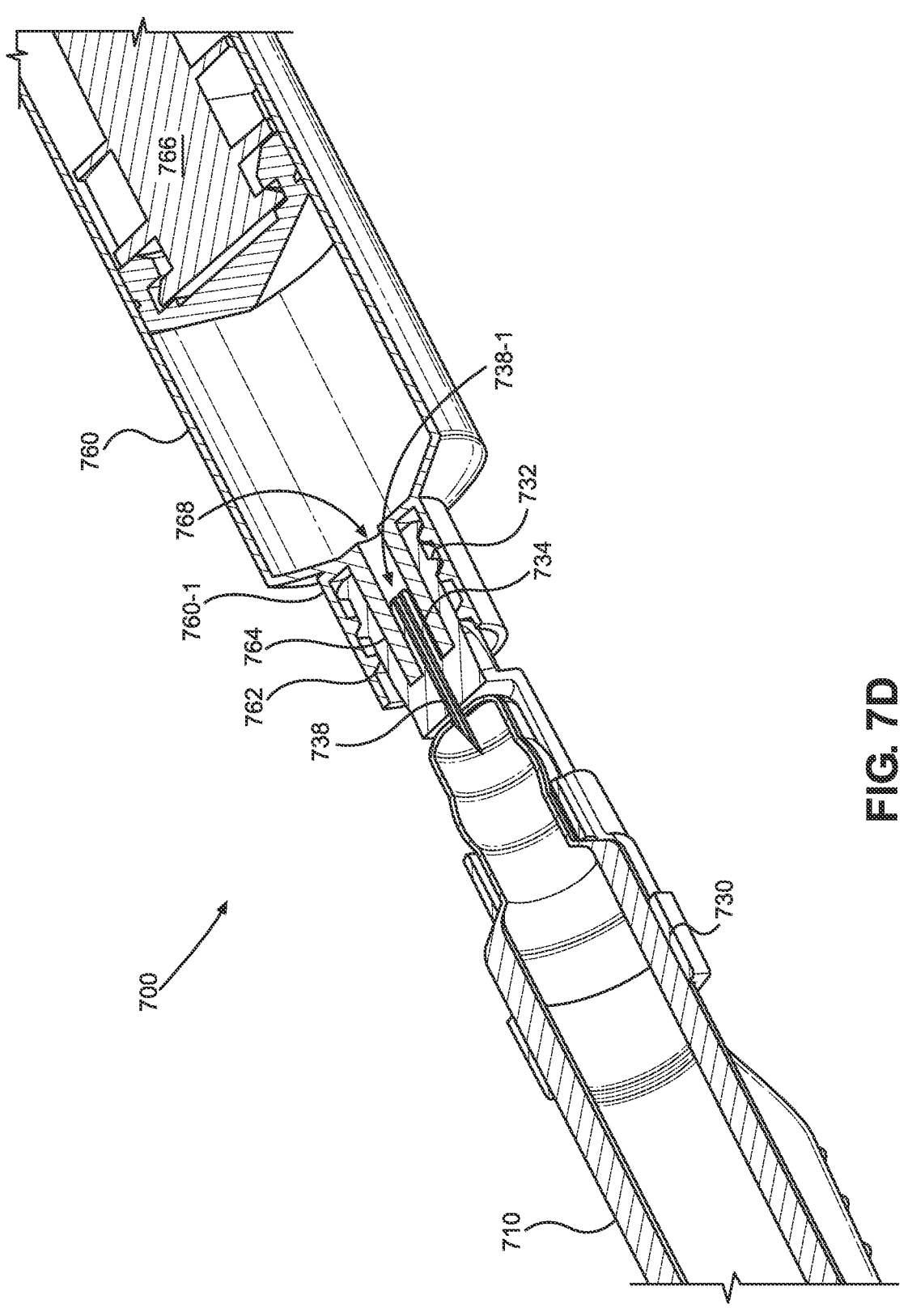
Figure 7F:
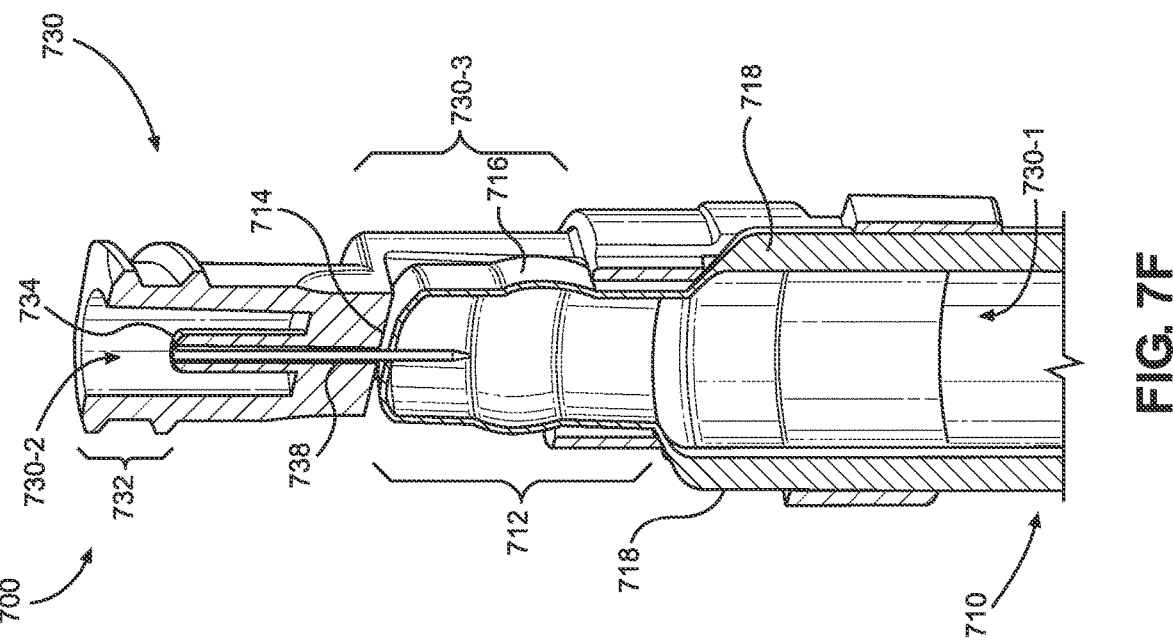
Figure 7E:
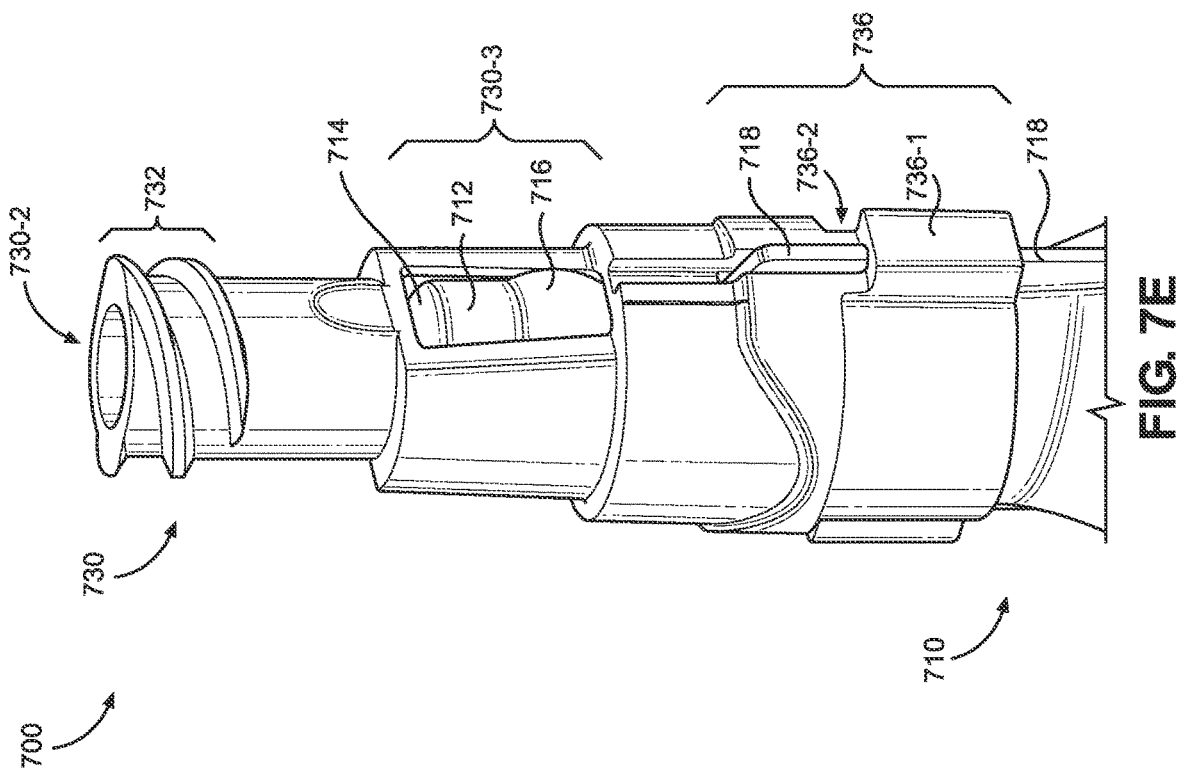

According to some embodiments, the neck 712 of the BFS bottle 710 may be visible through the aperture 730-3 even when the BFS bottle 710 is coupled to the connector 730. As shown in FIG. 7E and FIG. 7F, for example, the neck 712 and/or features thereof such as the seal 714 and/or the exterior rounded flange 716 may be visible through one or more apertures 730-3 (e.g., two (2) opposing and/or symmetrical apertures 730-3 as shown) so that a user may readily view and/or perceive whether the piercing element 738 has pierced the seal 714 and/or whether, e.g., during or after a dispensing action, any fluid remains in the BFS bottle 710 (e.g., in the neck 712 thereof in the case that the BFS bottle 710 and connector 730 are inverted such that gravity would force any remaining liquid into the neck 712).

In some embodiments, fewer or more components 710, 712, 714, 716, 718, 720, 730, 730-1, 730-2, 730-3, 732, 734, 736, 736-1, 736-2, 738, 738-1, 760, 760-1, 762, 764, 766, 768 and/or various configurations of the depicted components 710, 712, 714, 716, 718, 720, 730, 730-1, 730-2, 730-3, 732, 734, 736, 736-1, 736-2, 738, 738-1, 760, 760-1, 762, 764, 766, 768 may be included in the BFS connection system 700 without deviating from the scope of embodiments described herein. In some embodiments, the components 710, 712, 714, 716, 718, 720, 730, 730-1, 730-2, 730-3, 732, 734, 736, 736-1, 736-2, 738, 738-1, 760, 760-1, 762, 764, 766, 768 may be similar in configuration and/or functionality to similarly named and/or numbered components as described herein and/or may be utilized to conduct and/or facilitate methods, processes, and/or procedures described herein.

V. BFS Injection or Connection Assembly Medical Delivery Methods

In some embodiments, various methods and/or processes may be performed and/or implemented to utilize a BFS vial and/or bottle filled with a single dose of medicament (e.g., one or more therapeutic agents) to administer the single dose to a patient/target. In some embodiments, a method may cause a BFS bottle to be coupled to an administration component that is engaged to puncture the BFS vial and then may be utilized to inject (or otherwise administer) the medicament to the patient/target. According to some embodiments, a method may cause a BFS bottle to be coupled to a connection assembly, adaptor, and/or device that is engaged to puncture the BFS vial and then may be utilized to (i) transfer the medicament to a separate device, (ii) accept one or more fluids into the BFS bottle from another device, and/or (iii) accept fluid pressure and/or other forces applied to the contents of the BFS bottle via a connected device. The methods and/or processes (and/or diagrams and/or flow diagrams thereof) described herein do not necessarily imply a fixed order to any depicted actions, steps, and/or procedures, and embodiments may generally be performed in any order that is practicable unless otherwise and specifically noted. While the order of actions, steps, and/or procedures described herein is generally not fixed, in some embodiments, actions, steps, and/or procedures may be specifically performed in the order listed, depicted, and/or described and/or may be performed in response to any previously listed, depicted, and/or described action, step, and/or procedure.

In practice, for example, some or all of the following procedures may be followed to utilize a pre-filled medical delivery assembly to administer a medication (and/or other fluid) to a patient/target. In some embodiments, the area of injection may be cleaned and/or otherwise prepared. A neck and/or a fluid seal of the BFS bottle (e.g., a "first" part and/or component) may be cleaned (e.g., utilizing an alcohol wipe)

to prepare the BFS bottle for coupling to an administration component and/or assembly. In some embodiments, a "second" part and/or component comprising a pre-packaged mounting collar/coupling, needle hub (with an administration member), cap, and/or safety shield may comprise a seal that maintains an internal volume/fluid passage in a sterile state and the seal may be removed to prepare for the coupling to the BFS bottle. According to some embodiments, the administration assembly may be axially aligned with the neck of the BFS bottle and the neck may be inserted into the mounting collar (and/or through a base member of the safety shield) to engage a mounting flange with a cooperatively shaped mating feature of the BFS bottle. According to some embodiments, the administration component (and/or the mounting collar and/or the safety shield thereof) may "click" or snap onto the BFS bottle.

According to some embodiments, the BFS bottle may comprise one or more external angled flanges configured to travel in cooperative tracks and/or channels formed as threads on the mounting collar. In such a manner, for example, while manufacturing standard threads (e.g., as may exist on the mounting collar) on the BFS bottle may not be feasible, formation (e.g., molding) of the angled exterior flange(s) may permit the BFS bottle to be threaded into (or onto) a mounting collar with receiving threads. In some embodiments, a twist-off and/or other seal, e.g., having a grip portion permitting tactile gripping thereof, may be removed from the BFS bottle prior to mating of the BFS bottle with the mounting collar, connector, and/or other device. According to some embodiments, the mounting collar with receiving threads may comprise a needle hub that retains a needle. In some embodiments, a user may hold the mounting collar/needle hub with one hand/fingers and thread the mounting collar/needle hub onto the BFS bottle by applying rotational force thereto. In some embodiments, the rotational force may be applied to a cap installed on the mounting collar/needle hub. The cap may comprise an internal key that engages with the one or more stop and/or drive features of the needle hub, for example, to transfer the rotational force to the needle hub and accordingly advance the mating of the threads.

According to some embodiments, the cap may be removed to reveal the administration member and/or a first or administration end thereof. In some embodiments, the administration member (e.g., the administration end thereof) may be inserted into the patient and a collapsible reservoir of the BFS bottle may be squeezed (e.g., receive an application of radially inward force), thereby expelling the fluid through the administration member and into the patient. According to some embodiments, a syringe coupled to an opposite end of the BFS bottle may be utilized to provide fluid and/or fluid pressure that facilitates the administration. In some embodiments, the administration member may be withdrawn from the patient and/or a safety shield (e.g., coupled to and/or part of the administration component/assembly) may be selectively moved (e.g., flipped and/or rotated) into position to cover the administration member/needle. The pre-filled medical delivery assembly may then be properly disposed of. While the mounting collar and the needle hub are generally described and depicted as separate couplable objects, in some embodiments they may be manufactured (e.g., molded) as a single object or piece or may comprise additional pieces or parts.

VI. Multiple Inventive Embodiments Disclosed

Multiple inventive embodiments may be set forth and described in this disclose. Some embodiments may comprise and/or define various systems, methods, articles of manufacture, apparatus, and/or devices that are either stand-alone or may be utilized together. If described as stand-alone, this does not necessarily preclude interoperability with the other disclosed embodiments. Indeed, by being included in the same disclosure, Applicant has anticipated some degree of relation between the disclosed embodiments. If described as cooperative, this does not necessarily preclude stand-alone or alternative operability. Particularly with respect to described systems, for example, while various components are described in relation to their interoperability in some embodiments, in other embodiments one or more of such components may be operative to function without the other (and/or with another component, whether disclosed or not). As such, Applicant expressly reserves the right to pursue inventive material in accordance with any differently numbered set of figures, or combinations or portions thereof, in different application filings.

This disclosure may accordingly contain multiple inventive embodiments that may individually comprise inventive material, despite being described in certain embodiments with other inventive material. Different objects disclosed in different numbered figure sets, for example, may in some cases comprise different inventive components that alone constitute the broadest extents of the disclosure herein (e.g., with or without the other different numbered figure set components). In some embodiments, the combination and/or interaction of a subset of the components may comprise inventive subject matter. The interaction of the hub legs with the cone and/or piston leg tracks may, for example, be inventive with or without any of the other components. Similarly, the automatic misalignment of the needle and/or the legs may be effectuated by a subset of the components without the others being necessary.

In some embodiments, each of the separate components of the BFS injection/delivery system may comprise different and/or stand-alone inventions. The BFS bottle with one or more of the described features and/or components may comprise a first invention, for example, while the BFS connection assembly with one or more of the described features and/or components thereof may comprise a second invention, and/or while the needle hub or connector with one or more of the described features and/or components thereof may comprise a third invention. In some embodiments the different inventive subject matter and/or inventions may be utilized together in one or more combined systems or configurations (which themselves may be considered different inventive combinations) while in other embodiments the different inventive subject matter and/or inventions may be utilized separately from one another. Similarly, while each component described herein is described with respect to various possible features and/or configurations, each component may exist, in some embodiments, with only a single such described feature and/or configuration. The BFS bottles described herein may, for example, include only a fluid reservoir, while the assemblies and connectors may include only such features (e.g., ports and/or threads) that may be utilized to couple to a single separate device (e.g., a BFS bottle, syringe, etc.). In some embodiments, each separate set of drawings provided with the specification may comprise a separate and/or stand-alone invention.

VII. Rules of Interpretation

Throughout the description herein and unless otherwise specified, the following terms may include and/or encompass the example meanings provided. These terms and illustrative example meanings are provided to clarify the language selected to describe embodiments both in the specification and in the appended claims, and accordingly, are not intended to be generally limiting. While not generally limiting and while not limiting for all described embodiments, in some embodiments, the terms are specifically limited to the example definitions and/or examples provided. Other terms are defined throughout the present description.

As used herein, the term "coupled" may generally refer to any type or configuration of coupling that is or becomes known or practicable. Coupling may be descriptive, for example, of two or more objects, devices, and/or components that are communicatively coupled, mechanically coupled, electrically coupled, and/or magnetically coupled. The term "communicatively coupled" generally refers to any type or configuration of coupling that places two or more objects, devices, components, or portions, elements, or combinations thereof in communication. Mechanical, electrical, fluid, and magnetic communications are examples of such communications. The term "mechanically coupled" generally refers to any physical binding, adherence, attachment, and/or other form of physical contact between two or more objects, devices, components, or portions, elements, or combinations thereof. The term "electrically coupled" indicates that one or more objects, devices, components, or portions, elements, or combinations thereof, are in electrical contact such that an electrical signal, pulse, or current (e.g., electrical energy) is capable of passing between the one or more objects, enabling the objects to electrically communicate with one another. In some embodiments, electrical coupling may enable electrical energy to be transmitted wirelessly between two or more objects and/or devices. The term "magnetically coupled" indicates that one or more objects, devices, components, or portions, elements, or combinations thereof, are within one or more associated magnetic fields. Objects may be electrically and/or magnetically coupled without themselves being physically attached or mechanically coupled. For example, objects may communicate electrically through various wireless forms of communication or may be within (at least partially) a magnetic field, without being physically touching or even adjacent.

References to "interior" or "exterior" are references to areas and/or portions of an object with respect to other features such as holes, volumes, ports, passages, conduits, etc. Such objects necessarily comprise and/or define various "surfaces" such as an interior, exterior, inner, outer, inside, and/or outside surface. References to the different areas and/or portions are accordingly also references to the associated surfaces.

Numerous embodiments are described in this patent application, and are presented for illustrative purposes only. The described embodiments are not, and are not intended to be, limiting in any sense. The presently disclosed invention(s) are widely applicable to numerous embodiments, as is readily apparent from the disclosure. One of ordinary skill in the art will recognize that the disclosed invention(s) may be practiced with various modifications and alterations, such as structural, logical, software, and electrical modifications. Although particular features of the disclosed invention(s) may be described with reference to one or more particular embodiments and/or drawings, it should be understood that such features are not limited to usage in the one or more particular embodiments or drawings with reference to which they are described, unless expressly specified otherwise.

Devices that are in communication with each other need not be in continuous communication with each other, unless expressly specified otherwise.

A description of an embodiment with several components or features does not imply that all or even any of such components and/or features are required. On the contrary, a variety of optional components are described to illustrate the wide variety of possible embodiments of the present invention(s). Unless otherwise specified explicitly, no component and/or feature is essential or required.

Further, although process steps, algorithms or the like may be described in a sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention, and does not imply that the illustrated process is preferred.

The present disclosure provides, to one of ordinary skill in the art, an enabling description of several embodiments and/or inventions. Some of these embodiments and/or inventions may not be claimed in the present application, but may nevertheless be claimed in one or more continuing applications that claim the benefit of priority of the present application. Applicants intend to file additional applications to pursue patents for subject matter that has been disclosed and enabled but not claimed in the present application.

It will be understood that various modifications can be made to the embodiments of the present disclosure herein without departing from the scope thereof. Therefore, the above description should not be construed as limiting the disclosure, but merely as embodiments thereof. Those skilled in the art will envision other modifications within the scope of the invention as defined by the claims appended hereto.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The terms "including", "comprising" and variations thereof mean "including but not limited to", unless expressly specified otherwise.

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

The phrase "at least one of", when such phrase modifies a plurality of things (such as an enumerated list of things) means any combination of one or more of those things, unless expressly specified otherwise. For example, the phrase at least one of a widget, a car and a wheel means either (i) a widget, (ii) a car, (iii) a wheel, (iv) a widget and a car, (v) a widget and a wheel, (vi) a car and a wheel, or (vii) a widget, a car and a wheel.

The phrase "based on" does not mean "based only on", unless expressly specified otherwise. In other words, the phrase "based on" describes both "based only on" and "based at least on".

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

When an ordinal number (such as "first", "second", "third" and so on) is used as an adjective before a term, that ordinal number is used (unless expressly specified otherwise) merely to indicate a particular feature, such as to distinguish that particular feature from another feature that is described by the same term or by a similar term. For example, a "first widget" may be so named merely to distinguish it from, e.g., a "second widget". Thus, the mere usage of the ordinal numbers "first" and "second" before the term "widget" does not indicate any other relationship between the two widgets, and likewise does not indicate any other characteristics of either or both widgets. For example, the mere usage of the ordinal numbers "first" and "second" before the term "widget" (1) does not indicate that either widget comes before or after any other in order or location; (2) does not indicate that either widget occurs or acts before or after any other in time; and (3) does not indicate that either widget ranks above or below any other, as in importance or quality. In addition, the mere usage of ordinal numbers does not define a numerical limit to the features identified with the ordinal numbers. For example, the mere usage of the ordinal numbers "first" and "second" before the term "widget" does not indicate that there must be no more than two widgets.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A Blow-Fill-Seal (BFS) injection system comprising:
a) a BFS bottle, comprising:
    i) a radially compressible fluid reservoir storing a fluid content;
    ii) a first neck portion in fluid communication with the radially compressible fluid reservoir and formed at a first end of the BFS bottle;
    iii) a second neck portion in fluid communication with the radially compressible fluid reservoir and formed at a second end of the BFS bottle;
    iv) an angled exterior flange formed on an exterior of the first neck portion;
    v) a first fluid seal formed at the first end of the BFS bottle, the first fluid seal comprising a grip portion and defining a tear line between the grip portion and the first neck portion such that a shear force developed between the grip portion and the first neck portion causes the grip portion to separate from the BFS bottle and causes the first fluid seal to tear at the tear line, exposing the fluid content of the radially compressible reservoir at the first end of the BFS bottle;
    vi) a mounting feature formed proximate to the second end; and
    vii) a second fluid seal formed at the second end, the second fluid seal defining a radially planar piercing surface.

2. The BFS injection system of claim 1, further comprising:
b) a needle hub defining a first hub end and a second hub end, the first hub end defining a mounting socket comprising interior threads into which, in the case that the first fluid seal is separated from the BFS bottle at the tear line, the angled exterior flange is axially and rotationally mated, and the second hub end being coupled to a needle such that an application of radially inward force to the radially compressible fluid reservoir expels a dose of fluid stored in the radially compressible fluid reservoir through the needle.

3. The BFS injection system of claim 2, wherein the angled exterior flange comprises two angled exterior flanges disposed on opposite sides of the first neck portion and wherein each of the two angled exterior flanges extends between one quarter and one third along an outer circumference of the first neck portion.

4. The BFS injection system of claim 2, wherein the first neck portion defines a first exterior diameter at the angled exterior flange and defines a second exterior diameter between the angled exterior flange and the radially compressible fluid reservoir, and wherein the second exterior diameter is less than the first exterior diameter.

5. The BFS injection system of claim 4, wherein the first neck portion comprises, at the second exterior diameter, an axial rib connecting the radially compressible fluid reservoir to the first neck portion, and wherein the axial rib extends radially outward from the second exterior diameter to the first exterior diameter.

6. The BFS injection system of claim 1, further comprising:

b) a BFS connection assembly comprising:

i) a BFS port formed at a first assembly end, the BFS port comprising a seat configured to accept the mounting feature of the BFS bottle in the case that the second end of the BFS bottle is inserted into the BFS port;

ii) an outlet port formed at a second assembly end, the outlet port comprising threads;

iii) a projection extending axially from a first projection end at an interior extent of the outlet port, the projection defining a fluid outlet at a second projection end thereof; and iv) a tubular piercing element coupled within the projection and connecting the fluid outlet to the BFS port, wherein the tubular piercing element is disposed to pierce the second fluid seal of the BFS bottle in the case that the second end of the BFS bottle is inserted into the BFS port.

7. The BFS injection system of claim 6, wherein the projection comprises a cone.

8. The BFS injection system of claim 7, wherein the cone is tapered from the first projection end to the second projection end.

9. The BFS injection system of claim 6, wherein the threads of the outlet port comprise interior threads formed within the outlet port.

10. The BFS injection system of claim 6, wherein the threads of the outlet port comprise exterior threads formed on an outside surface of the outlet port.

11. The BFS injection system of claim 6, wherein the tubular piercing element comprises a metal tube disposed in an interior channel of the projection and a proximate end of the metal tube is beveled to form a point that extends axially into the BFS port.

12. The BFS injection system of claim 6, wherein the seat comprises an axial track and wherein the mounting feature of the BFS bottle comprises an axial exterior flange.

* * * * *